United States Patent
Chang et al.

(10) Patent No.: US 6,919,350 B2
(45) Date of Patent: Jul. 19, 2005

(54) COMPOSITIONS AND METHODS FOR REDUCING RESPIRATORY DEPRESSION AND ATTENDANT SIDE EFFECTS OF MU OPIOID COMPOUNDS

(75) Inventors: Kwen-Jen Chang, Chapel Hill, NC (US); Robert W. McNutt, Jr., Durham, NC (US); Hugh O. Pettit, Cary, NC (US); Michael J. Bishop, Durham, NC (US)

(73) Assignee: Ardent Pharmaceuticals, Inc., Durham, NC (US)

( * ) Notice: Subject to any disclaimer, the term of this patent is extended or adjusted under 35 U.S.C. 154(b) by 289 days.

(21) Appl. No.: 09/974,004

(22) Filed: Oct. 9, 2001

(65) Prior Publication Data

US 2002/0111359 A1 Aug. 15, 2002

Related U.S. Application Data

(60) Division of application No. 09/352,308, filed on Jul. 12, 1999, now Pat. No. 6,300,332, which is a division of application No. 08/887,312, filed on Jul. 3, 1997, now Pat. No. 5,985,880, which is a continuation-in-part of application No. 08/658,726, filed on Jun. 5, 1996, now Pat. No. 5,801,858.

(51) Int. Cl.[7] .................... A61K 31/44; A61K 31/4965; A61K 38/00; A61K 31/445
(52) U.S. Cl. .................... 514/282; 514/12; 514/255.04; 514/317; 514/331
(58) Field of Search ........................... 514/282, 255.04, 514/12, 317, 331

(56) References Cited

U.S. PATENT DOCUMENTS

| | | |
|---|---|---|
| 5,552,404 A | 9/1996 | Chang et al. |
| 5,574,159 A | 11/1996 | Chang et al. |
| 5,658,908 A | 8/1997 | Chang et al. |
| 5,681,830 A | 10/1997 | Chang et al. |
| 5,807,858 A | 9/1998 | Chang et al. |
| 5,854,249 A | 12/1998 | Chang et al. |
| 5,968,551 A | 10/1999 | Oshlack et al. ............. 424/456 |
| 5,985,880 A | 11/1999 | Chang et al. |
| 6,200,978 B1 | 3/2001 | Maw et al. |
| 6,300,332 B1 | 10/2001 | Chang et al. |

FOREIGN PATENT DOCUMENTS

| | | |
|---|---|---|
| HU | 208633 | 5/1994 |
| HU | 218673 | 10/2000 |
| WO | WO 98/52929 | 11/1998 |

OTHER PUBLICATIONS

Database CAPLUS on STN, Dep. Pharmacology, University Michigan, (Ann Arbor, MI), Document No. 121:271967, Negus, S. et al., "Behavioral effects of the systematically active delta opioid agonist BW373U86 in rhesus monkeys," abstract, J. Pharmacol. Exp. Ther., 270(3), 1025–1034, 1994.

Primary Examiner—Kevin E. Weddington
(74) Attorney, Agent, or Firm—Marianne Fuierer; Steven J. Hultquist

(57) ABSTRACT

A method of reducing, treating or preventing drug-mediated respiratory depression, muscle rigidity, or nausea/vomiting in an animal, incident to the administration to said animal of a mixed delta/mu opioid agonist or a respiratory depression-mediating drug, comprising administering to the animal receiving said drug an effective amount of a delta receptor agonist compound. Preferred examples of such delta receptor agonist compound include diarylmethyl piperazine compounds and diarylmethyl piperidine compounds, and pharmaceutical compositions thereof, having utility in medical therapy for reducing respiratory depression associated with certain analgesics, such as mu opiates.

29 Claims, 2 Drawing Sheets

COMPOSITIONS AND METHODS FOR REDUCING RESPIRATORY DEPRESSION AND ATTENDANT SIDE EFFECTS OF MU OPIOID COMPOUNDS

CROSS-REFERENCE TO RELATED APPLICATIONS

This is a divisional application of U.S. patent application Ser. No. 09/352,308 filed Jul. 12, 1999 and issued Oct. 9, 2001 as U.S. Pat. No. 6,300,332, which is a divisional of U.S. patent application Ser. No. 08/887,312 filed Jul. 3, 1997, now U.S. Pat. No. 5,985,880, which is a continuation-in-part of U.S. patent application Ser. No. 08/658,726, filed Jun. 5, 1996 now U.S. Pat. No. 5,801,858. The disclosures of the following applications are hereby incorporated herein by reference in their entirety: U.S. patent application Ser. No. 08/658,726 filed Jun. 5, 1996; U.S. patent application Ser. No. 08/169,879 filed Dec. 17, 1993; U.S. patent application Ser. No. 08/098,333 filed Jul. 30, 1993; U.S. patent application Ser. No. 08/430,677 filed Apr. 28, 1995; International Patent Application No. PCT/GB93/00216 filed Feb. 2, 1993; Great Britain patent application 9202238.3 filed 3 Feb. 1992; and all applications from which they claim priority, or from which priority is claimed.

This invention relates generally to methods for reducing, treating, reversing or preventing drug-mediated respiratory depression, such as may be directly or indirectly caused by use of various bioactive compositions, including anaesthetics, barbiturates, analgesics, etc. The invention further relates to diarylmethyl piperazine compounds and diarylmethyl piperidine compounds, and pharmaceutical compositions thereof, having utility in medical therapy especially for reducing respiratory depression associated with certain analgesics, such as mu opiates. This invention additionally relates to diarylmethyl piperazine compounds and diarylmethyl piperidine compounds having utility in assays for determining the respiratory reducing characteristics of other bioactive compounds, including other diarylmethyl piperazine compounds and other diarylmethyl piperidine compounds.

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opiate receptors.

Opioid drugs typically are classified by their binding selectivity in respect of the cellular and differentiated tissue receptors to which a specific drug species binds as a ligand. These receptors include mu ($\mu$), delta ($\delta$), sigma ($\sigma$) and kappa ($\kappa$) receptors.

The well-known narcotic opiates, such as morphine and its analogs, are selective for the opiate mu receptor. Mu receptors mediate analgesia, respiratory depression, and inhibition of gastrointestinal transit. Kappa receptors mediate analgesia and sedation. Sigma receptors mediate various biological activities.

Diarylmethyl piperazine compounds and diarylmethyl piperidine compounds having utility, for example, as analgesics, are disclosed in International Publication WO93/15062, which is incorporated by reference herein in its entirety. The present application provides for the use of compounds of such general type to treat or prevent respiratory depression.

Campa, M. J., et al., "Characterization of $\delta$ Opioid Receptors in Lung Cancer Using a Novel Nonpeptidic Ligand," Cancer Research 56, 1965–1701, Apr. 1, 1996, describes binding of [$^3$H] (+)-4-[($\alpha$-R)-$\alpha$-((2S,5R)-4-allyl-2,5-dimethyl-1-piperazinyl)-3-hydroxybenzyl)-N,N-diethylbenzamide with membranes prepared from various small cell lung cancer cells.

There is a continuing need in the art for methods of preventing or treating respiratory depression associated with the use of various bioactive compositions, e.g., certain analgesics, anaesthetics, and barbiturates, which effect respiratory depression, either directly or indirectly.

There is also a continuing need for improved opioid compounds, particularly compounds which can reduce respiratory depression associated with the use of certain analgesics, such as mu opiate analgesic compounds, when such improved opioid compounds are administered contemporaneously with or sequential to the administration of the respiratory depression-mediating analgesic.

It is an object of the present invention to provide a bioactive compound which when administered contemporaneously with analgesics, anesthetics, barbiturates and other drugs which cause respiratory depression, acts to markedly attenuate such respiratory depression side effects.

SUMMARY OF THE INVENTION

The present invention relates to methods of treating, reducing or preventing respiratory depression in an animal, e.g., a human or non-human mammal, comprising administering to such animal an effective amount of a composition comprising a delta receptor agonist, optionally further including a mu receptor agonist compound.

Illustrative examples of suitable delta receptor agonist compounds that may be co-administered in accordance with the invention include, but are not limited to:

(+)-4-(($\alpha$R)-$\alpha$-((2S,5R)-4-allyl-2,5-dimethyl-1-piperazinyl)-3-hydroxybenzyl)-N,N-diethylbenzamide;

[D-Pen$^2$,D-Pen$^5$]-(enkephalin);

deltorphin I;

deltorphin II;

the compounds disclosed in International Patent Application Publication WO96/36620 published 21 Nov. 1996 for "Diaryldiamine Derivatives and Their Use as Delta Opioid (ant)-agonists," the disclosure of which is hereby incorporated herein by reference; and the compounds disclosed in International Patent Application Publication WO97/10230 published 20 Mar. 1997 for "Diarylalkenylamine Derivatives," the disclosure of which is hereby incorporated herein by reference.

Particularly preferred delta agonist compounds from among the foregoing illustrative compounds include

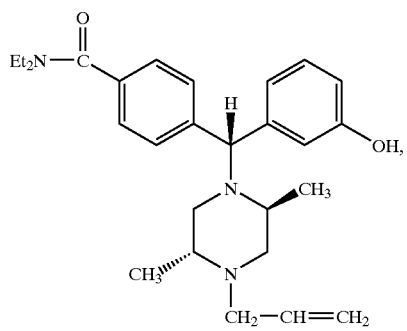

(+)-4-(($\alpha$R)-$\alpha$-((2S,5R)-4-allyl-2,5-dimethyl-1-piperazinyl)-3-hydroxybenzyl)-N,N-diethylbenzamide, and (±)-4-((αR*)-α-((2R*,5S*)-4-allyl-2,5-dimethyl-1-piperazinyl)-3-hydroxybenzyl)-N,N-dimethylbenzenesulfonamide (and, independently, each of the component isomers thereof, viz., (+)-4-((αR)-α-((2R,5S)-4-allyl-2,5-dimethyl-1-piperazinyl)-3-hydroxybenzyl)-N,N-dimethylbenzenesulfonamide, and (−)-4-((αR)-α-((2R,5S)-4-allyl-2,5-dimethyl-1-piperazinyl)-3-hydroxybenzyl)-N,N-dimethylbenzenesulfonamide).

The composition that is co-administered with the bioactive agent mediating respiratory depression may further include a mu receptor agonist such as morphine, fentanyl, alfentanil and their analogs, or the mu receptor agonists disclosed in U.S. patent application Ser. No. 08/284,445 and U.S. patent application Ser. No. 08/285,313, the disclosures of which hereby are incorporated herein by reference, including compounds therein displaying predominantly mu receptor agonist character, as well as compounds therein disclosed displaying mixed mu/delta receptor agonism. Examples of compounds displaying such mixed mu/delta agonist character include by way of example the following compounds:

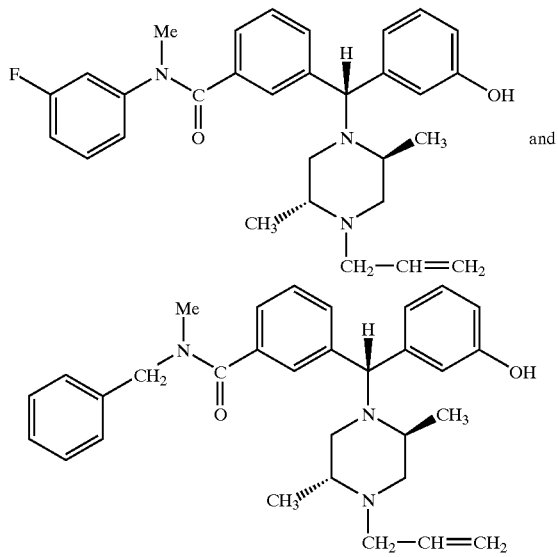

and

The compounds mediating respiratory depression, as mentioned above, include various analgesics, and asthetics, and barbiturates, such as for example morphine, fentanyl, midazolam, meperidine, sufentanil and codeine.

Thus, the invention contemplates co-administration with drug agents mediating respiratory depression, of delta receptor agonist compounds, optionally with further co-administration of mu receptor agonist agents, or simply compounds displaying mixed mu receptor/delta receptor agonist character, in an amount effective to combat, e.g., significantly attenuate, and preferably substantially eliminate, the respiratory depression incident to the use of the respiratory depression-mediating agent.

The invention therefore has broad utility in surgical and clinical care applications, to combat the unwanted respiratory depression side effect incident to the use of such commonly used drugs as morphine and fentanyl.

Illustrative of a preferred class of delta agonist compounds which may be usefully employed in the broad practice of the present invention are delta agonist compounds of the formula:

| Compound | Delta Receptor IC$_{50}$ (nM) | Mouse Vas Deferens ED$_{50}$ (nM) |
|---|---|---|
| 1 | 2[a] | 43 |
| 2 | 1[a] | — |
| 3 | — | — |
| 4 | — | >1,000 |
| 5 | 1.6 | 260 |
| 6 | 4.0 | 25 |
| 7 | 1.1 | 560 |
| 8 | 0.86 | 30 |
| 9 | 1.5 | 450 |
| 10 | 1.1 | 90 |
| 11 | — | — |
| 12 | 1.2 | 250 |
| 13 | 0.3 | 200 |
| 14 | 2 | pA$_2$ = 7.1[b] |
| 15 | 2.8 | pA$_2$ = 7.0[b] |
| 16 | 3.1 | pA$_2$ = 7.2[b] |
| 17 | 1.5 | pA$_2$ = 8.2[c] |
| 18 | 1.3 | 250 |
| 19 | 2.6 | 37 |
| 20 | 1.3 | 78 |
| 21 | 1.6 | 44 |
| 22 | 0.7 | 4400 |
| 23 | 3.3 | 42 |
| 24 | 2.3 | 20 | wherein:

Ar is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent R$^1$, Y is selected from the group consisting of:

hydrogen;

halogen;

$C_1$–$C_6$ alkyl, $C_2$–$C_6$ alkenyl, $C_2$–$C_6$ alkynyl;

$C_1$–$C_6$ haloalkyl;

$C_1$–$C_6$ alkoxy;

$C_3$–$C_6$ cycloalkoxy;

sulfides of the formula SR$^8$ where R$^8$ is $C_1$–$C_6$ alkyl, $C_2$–$C_6$ alkenyl, $C_2$–$C_6$ alkynyl, $C_3$–$C_6$ cycloalkyl, arylalkyl having a $C_5$–$C_{10}$ aryl moiety and an $C_1$–$C_6$ alkyl moiety, or $C_5$–$C_{10}$ aryl;

sulfoxides of the formula SOR$^8$ where R$^8$ is the same as above;

sulfones of the formula SO$_2$R$^8$ where R$^8$ is the same as above;

nitrile;

$C_1$–$C_6$ acyl;

alkoxycarbonylamino (carbamoyl) of the formula NHCO$_2$R$^8$ where R$^8$ is the same as above;

carboxylic acid, or an ester, amide, or salt thereof;

aminomethyl of the formula CH$_2$NR$^9$R$^{10}$ where R$^9$ and R$^{10}$ may be the same or different, and may be hydrogen, $C_1$–$C_6$ alkyl, $C_2$–$C_6$ alkenyl, $C_2$–$C_6$ alkynyl, $C_2$–$C_6$ hydroxyalkyl, $C_2$–$C_6$ methoxyalkyl, $C_3$–$C_6$ cycloalkyl, or $C_5$–$C_{10}$ aryl, or R$^9$ and R$^{10}$ together may form a ring of 5 or 6 atoms, the ring atoms selected from the group consisting of N and C;

carboxamides of the formula CONR$^9$R$^{10}$ where R$^9$ and R$^{10}$ are the same as above, or $C_2$–$C_{30}$ peptide conjugates thereof; and sulfonamides of the formula SO$_2$NR$^9$R$^{10}$ where R$^9$ and R$^{10}$ are the same as above;

Z is selected from the group consisting of:
hydroxyl, and esters thereof;
hydroxymethyl, and esters thereof; and
amino, and carboxamides and sulfonamides thereof;
G is carbon or nitrogen;
$R^1$ is hydrogen, halogen, or $C_1$–$C_4$ alkyl, $C_2$–$C_4$ alkenyl, $C_1$–$C_4$ alkynyl;
$R^2$ is hydrogen, halogen, or $C_1$–$C_4$ alkyl, $C_2$–$C_4$ alkenyl, $C_1$–$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
hydrogen;
$C_1$–$C_6$ alkyl, $C_2$–$C_6$ alkenyl, $C_2$–$C_6$ alkynyl;
$C_3$–$C_6$ cycloalkyl;
arylalkyl having $C_5$–$C_{10}$ aryl and $C_1$–$C_6$ alkyl moieties;
alkoxyalkyl having $C_1$–$C_4$ alkoxy and $C_1$–$C_4$ alkyl moieties;
$C_2$–$C_4$ cyanoalkyl;
$C_2$–$C_4$ hydroxyalkyl;
aminocarbonylalkyl having a $C_1$–$C_4$ alkyl moiety; and
$R^{12}COR^{13}$, where $R^{12}$ is $C_1$–$C_4$ alkylene, and $R^{13}$ is $C_1$–$C_4$ alkyl or $C_1$–$C_4$ alkoxy; and
$R^7$ is hydrogen or fluorine,
or a pharmaceutically acceptable ester or salt thereof.

In addition to methods of treating, reducing or preventing respiratory depression, the present invention also contemplates methods for screening and characterizing opioid compounds that reduce, treat or prevent respiratory depression.

The methods for screening such opioid compounds (i.e., opioid compounds that reduce, treat or prevent respiratory depression, referred to here as respiratory depression-suppressing compounds) comprise conducting activity reversal assays of candidate respiratory depression-suppressing compounds in receptor tissue to determine if such candidate compounds transductionally mediate a respiratory depression effect in response to a respiration-depressing composition. Such activity reversal assays are conducted comparatively, in the absence and in the presence of an anti-suppression compound of formula (I), i.e., a compound combatting the respiratory depression-supressing effect and allowing such respiratory depression to take place. If the activity of the candidate compound is markedly reversed in the receptor system by the presence of the anti-suppression compound of formula (I), the assay is positive for the candidate respiratory depression-suppressing compound, indicating its potential bioefficacy for supressing respiratory depression effects incident to the use of other therapeutic agents.

The anti-suppression compound of formula (I) employed in the above-described screen assay is preferably selected from those of the group consisting of:
(−)-4-((αS)-α-((2R,5R)-4-allyl-2,5-dimethyl-1-piperazinyl)-3-hydroxybenzyl)-N,N-diethylbenzamide;
(−)-4-((αS)-α-((2R,5R)-2,5-dimethyl-4-propyl-1-piperazinyl)-3-hydroxybenzyl)-N,N-diethylbenzamide;
cis-4-(α-(4-((Z)-2-butenyl)-3,5-dimethyl-1-piperazinyl)-3-hydroxybenzyl)-N,N-diethylbenzamide; and
acceptable salts thereof. In such context, the term "acceptable" in reference to suitable salt species of the particular identified compounds, means salts which are effective to mediate suppression of respiratory depression effects.

Further, the present invention provides pharmaceutical compositions comprising a combination of an effective amount of an opiate analgesic and an effective amount of a composition for combatting the respiratory depression effect of a respiratory depression-mediating agent.

The respiratory depression-combatting agent comprise at least one delta receptor agonist compound.

The delta agonist compound employed in the invention may also exhibit mu receptor agonism (i.e., such compound may have mixed mu/delta receptor agonist character) or the respiratory depression-combatting composition of the invention may include different compounds, one or more of which exhibits delta receptor agonist character, and one or more different ones of which exhibit mu receptor agonist character.

As a still farther alternative, the respiratory depression-combatting composition of the invention may utilize two or more compounds, each of which has a varying mu/delta receptor agonist activity character.

In a specific embodiment, the invention contemplates as the respiratory depression-combatting compound, a compound of formula (I) for reducing, treating or preventing respiratory depression which would otherwise be effected by an administered opiate analgesic.

Additionally, the present invention provides the following particularly preferred compounds, which can be included, for example, in a pharmaceutical composition containing a compound and a pharmaceutically acceptable carrier, and can be used, for example, in a form suitable for injectable or spinal administration, to combat respiratory depression incident to the use of analgesic or anesthetic agents. The particularly preferred compounds are as follows:
(−)-4-((αR)-α-((2R,5R)-4-allyl-2,5-dimethyl-1-piperazinyl)-3-hydroxybenzyl)-N,N-diethylbenzamide;
(−)-4-((αR)-α-((2R,5R)-2,5-dimethyl-4-propyl-1-piperazinyl)-3-hydroxybenzyl)-N,N-diethylbenzamide;
4-((αR)-α-(2S,5S)-4-allyl-2,5-dimethyl-1-piperazinyl)-3-hydroxybenzyl)benzamide;
(±)-3-((αR*)-α-((2S*,5R*)-4-allyl-2,5-dimethyl-1-piperazinyl)-3-hydroxybenzyl)benzamide;
N,N-diethyl-4-((αR)-3-hydroxy-α-((2R,5R)-2,5-dimethyl-1-piperazinyl)benzyl)benzamide;
4-((αR)-α-((2S,5S)-4-allyl-2,5-dimethyl-1-piperazinyl)-3-hydroxybenzyl)-N-ethyl-N-methylbenzamide;
3-((αR)-α-((2S,5S)-4-ally-2,5-dimethyl-1-piperazinyl)benzyl)phenol;
3-((αS)-α-((2S,5S)-4-allyl-2,5-dimethyl-1-piperazinyl)benzyl)phenol;
(±)-4-((αR*)-α-((2R*,5S*)-4-allyl-2,5-dimethyl-1-piperazinylbenyl)-3-hydroxybenzyl)-N,N-dimethylbenzenesulfonamide;
(+)-4-((αR)-α-((2R,5S)-4-allyl-2,5-dimethyl-1-piperazinyl)-3-hydroxybenzyl)-N,N-dimethylbenzenesulfonamide;
(−)-4-((αR)-α-((2R,5S)-4-allyl-2,5-dimethyl-1-piperazinyl)-3-hydroxybenzyl)-N,N-dimethylbenzenesulfonamide);
(±)-N,N-diethyl-4-((αR*)-3-hydroxy-α-((2R*,5S*)-2,4,5-trimethyl-1-piperazinyl)benzyl)benzamide;
(+)-4-((αS)-α-((2S,5S)-4-allyl-2,5-dimethyl-1-piperazinyl)-3-hydroxybenzyl)-N,N-diethylbenzamide; and
pharmaceutically acceptable salts thereof.

These preferred compounds of the invention have utility in medical therapy, in particular for reducing, treating or preventing respiratory depression associated with certain analgesics, such as mu opiates.

Various other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1A:
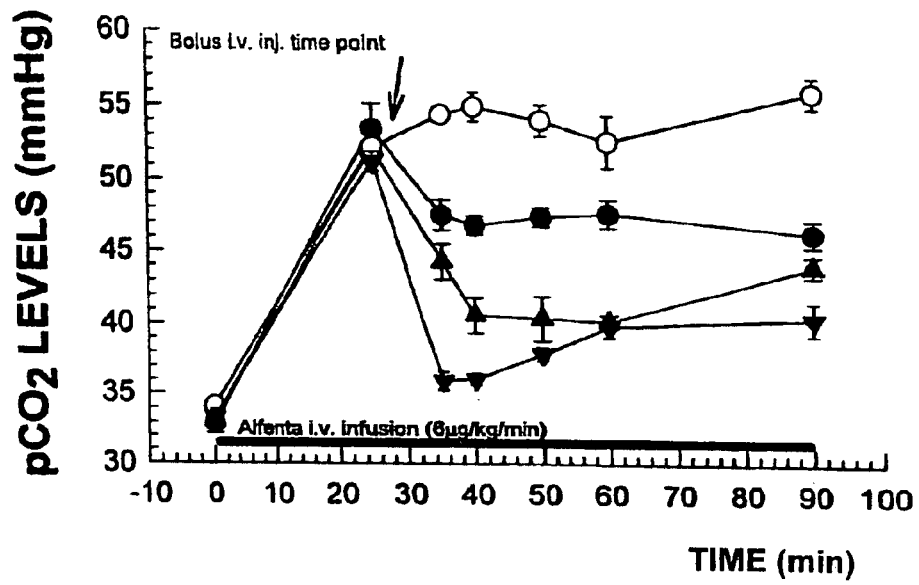
FIG. 1A shows the effect of the positive isomer of the delta agonist BW373U86 on respiratory depression induced by the mu agonist, alfenta.

The vast majority of currently used high potency analgesics, including morphine, fentanyl, meperidine, sufentanil, codeine and naltrindole, are mu receptor binding compounds. As is well established, these compounds, while highly efficacious for mediating analgesia, have accompanying side effects, including respiratory depression. The use of delta agonist compounds according to the present invention may prevent, reduce, attenuate or even eliminate or reverse conditions in which analgesia induces respiratory depression, such as the respiratory depressing side effects normally attendant to the use of mu receptor binding compounds.

The present invention therefore provides, inter alia, methods of reducing, treating or preventing respiratory depression using respiratory depression-combatting agents including delta agonist compound(s). Such delta agonist compounds may as mentioned exhibit mixed mu/delta receptor agonist character, or be provided with other receptor binding agents exhibiting mu receptor agonism. The compositions of the invention therefore may be co-administered with drugs or other bioactive agents which mediate respiratory depression, so that the respiratory depression effects of such drug or bioactive agent are at least partially attenuated.

The delta agonist compounds which may be usefully employed in such compositions include delta agonist compounds and pharmaceutical compositions comprising a combination of an effective amount of an opiate analgesic and an amount of a delta agonist compound effective for reducing, treating or preventing respiratory depression. The use of delta agonist compounds for combatting respiratory depression, and in combination pharmaceutical compositions, are more fully discussed below.

Preferably, the delta agonist compound reduces, treats or prevents respiratory depression without affecting analgesia desired from opiate analgesic agents, such as mu opiate analgesic agents.

Delta agonist compounds potentially useful in the broad practice of the present invention variously include:
I. [D-Pen$^2$,D-Pen$^5$]-(enkephalin);
II. deltorphin I;
III. deltorphin II;
IV. delta agonist compounds of the formula:

| Compound | Delta Receptor IC$_{50}$ (nM) | Mouse Vas Deferens ED$_{50}$ (nM) |
|---|---|---|
| 1 | 2$^a$ | 43 |
| 2 | 1$^a$ | — |
| 3 | — | — |
| 4 | — | >1,000 |
| 5 | 1.6 | 260 |
| 6 | 4.0 | 25 |
| 7 | 1.1 | 560 |
| 8 | 0.86 | 30 |
| 9 | 1.5 | 450 |
| 10 | 1.1 | 90 |
| 11 | — | — |
| 12 | 1.2 | 250 |
| 13 | 0.3 | 200 |
| 14 | 2 | pA$_2$ = 7.1$^b$ |
| 15 | 2.8 | pA$_2$ = 7.0$^b$ |
| 16 | 3.1 | pA$_2$ = 7.2$^b$ |
| 17 | 1.5 | pA$_2$ = 8.2$^c$ |
| 18 | 1.3 | 250 |
| 19 | 2.6 | 37 |
| 20 | 1.3 | 78 |
| 21 | 1.6 | 44 |
| 22 | 0.7 | 4400 |
| 23 | 3.3 | 42 |
| 24 | 2.3 | 20 | wherein:

Ar is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent R$^1$, Y is selected from the group consisting of:

hydrogen;

halogen;

C$_1$–C$_6$ alkyl, C$_2$–C$_6$ alkenyl, C$_2$–C$_6$ alkynyl;

C$_1$–C$_6$ haloalkyl;

C$_1$–C$_6$ alkoxy;

C$_3$–C$_6$ cycloalkoxy;

sulfides of the formula SR$^8$ where R$^8$ is C$_1$–C$_6$ alkyl, C$_2$–C$_6$ alkenyl, C$_2$–C$_6$ alkynyl, C$_3$–C$_6$ cycloalkyl, arylalkyl having a C$_5$–C$_{10}$ aryl moiety and an C$_1$–C$_6$ alkyl moiety, or C$_5$–C$_{10}$ aryl;

sulfoxides of the formula SOR$^8$ where R$^8$ is the same as above;

sulfones of the formula SO$_2$R$^8$ where R$^8$ is the same as above;

nitrite;

C$_1$–C$_6$ acyl;

alkoxycarbonylamino (carbamoyl) of the formula NHCO$_2$R$^8$ where R$^8$ is the same as above;

carboxylic acid, or an ester, amide, or salt thereof;

aminomethyl of the formula CH$_2$NR$^9$R$^{10}$ where R$^9$ and R$^{10}$ may be the same or different, and may be hydrogen, C$_1$–C$_6$ alkyl, C$_2$–C$_6$ alkenyl, C$_2$–C$_6$ alkynyl, C$_2$–C$_6$ hydroxyalkyl, C$_2$–C$_6$ methoxyalkyl, C$_3$–C$_6$ cycloalkyl, or C$_5$–C$_{10}$ aryl, or R$^9$ and R$^{10}$ together may form a ring of 5 or 6 atoms, the ring atoms selected from the group consisting of N and C;

carboxamides of the formula CONR$^9$R$^{10}$ where R$^9$ and R$^{10}$ are the same as above, or C$_2$–C$_{30}$ peptide conjugates thereof; and sulfonamides of the formula SO$_2$NR$^9$R$^{10}$ where R$^9$ and R$^{10}$ are the same as above;

Z is selected from the group consisting of:

hydroxyl, and esters thereof;

hydroxymethyl, and esters thereof; and amino, and carboxamides and sulfonamides thereof;

G is carbon or nitrogen;

$R^1$ is hydrogen, halogen, or $C_1$–$C_4$ alkyl, $C_2$–$C_4$ alkenyl, $C_1$–$C_4$ alkynyl;

$R^2$ is hydrogen, halogen, or $C_1$–$C_4$ alkyl, $C_2$–$C_4$ alkenyl, $C_1$–$C_4$ alkynyl;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;

$R^6$ is selected from the group consisting of:

hydrogen;

$C_1$–$C_6$ alkyl, $C_2$–$C_6$ alkenyl, $C_2$–$C_6$ alkynyl;

$C_3$–$C_6$ cycloalkyl;

arylalkyl having $C_5$–$C_{10}$ aryl and $C_1$–$C_6$ alkyl moieties;

alkoxyalkyl having $C_1$–$C_4$ alkoxy and $C_1$–$C_4$ alkyl moieties;

$C_2$–$C_4$ cyanoalkyl;

$C_2$–$C_4$ hydroxyalkyl;

aminocarbonylalkyl having a $C_1$–$C_4$ alkyl moiety; and $R^{12}COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine, or a pharmaceutically acceptable ester or salt thereof;

V. Delta Agonist Compounds of the Formula:

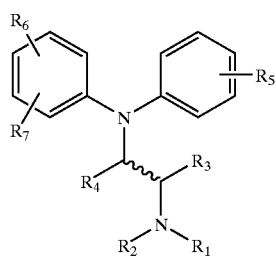

in which, $R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen.

$R_3$ and $R_4$, which can be the same or different, are each hydrogen, linear or branched $C_{1-6}$ alkyl, or $R_4$ is oxygen forming with the carbon atom to which is attached a C=O group;

$R_5$ is hydrogen, hydroxy, $C_{1-3}$ alkoxy, thiol or alkylthio;

$R_6$ is phenyl, halogen, $NH_2$ or a para or meta —C(Z)-R group, in which Z is oxygen or sulphur;

$R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or R is a para or metal

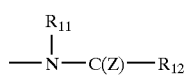

group in which $R_{11}$ and $R_{12}$ which may the same or different are hydrogen, straight or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring, and Z is as defined above; and, $R_7$ is hydrogen, straight or branched $C_{1-8}$ alkyl or halogen; and VI. Delta Agonist Compounds of the Formula;

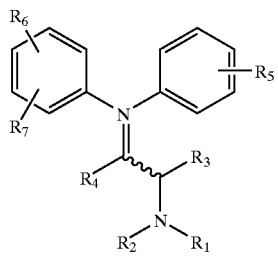

in which, $R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen.

$R_3$ and $R_4$, which can be the same or different, are each hydrogen, linear or branched $C_{1-6}$ alkyl;

$R_5$ is hydroxy, $C_{1-6}$ alkoxy, thiol or alkylthio;

$R_6$ is a —C(Z)-Rg group, in which Z is oxygen or sulphur, $R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or $R_6$ is a

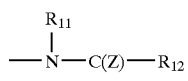

group in which $R_{11}$ and $R_{12}$ have the same meaning as $R_9$ and $R_{10}$ or together form an optionally substituted heterocyclic ring and Z is as defined above, and $R_7$ is hydrogen, straight or branched $C_{1-8}$ alkyl or halogen.

An illustrative delta agonist compound from among the foregoing illustrative compounds is:

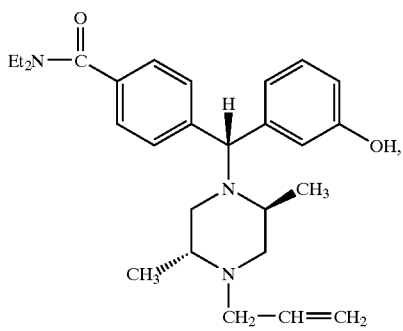

(+)-4-((αR)-α-((2S,5R)-4-allyl-2,5-dimethyl-1-piperazinyl)-3-hydroxybenzyl)-N,N-diethylbenzamide.

The composition that is co-administered with the bioactive agent mediating respiratory depression may further include a mu receptor agonist such as the mu receptor agonists disclosed in U.S. patent application Ser. No. 08/284,445 and U.S. patent application Ser. No. 08/285,313, including mu receptor agonist compounds, and mixed mu/delta receptor agonist compounds such as:

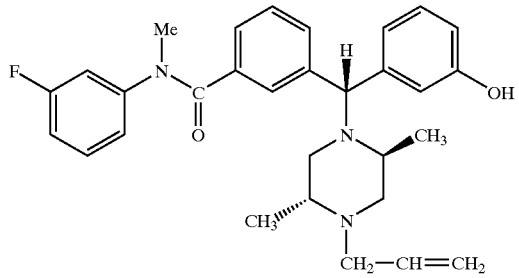

and

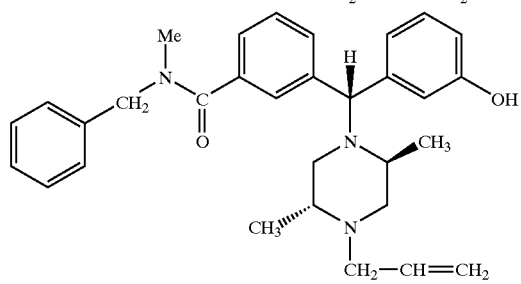

When the respiratory depression-combatting compound utilized in the practice of the invention does not affect analgesia, it can be used in combination with an analgesic opiate agent, so that the opiate agent produces its desired analgesic effect, but without the occurrence of the respiratory depression that otherwise (i.e., in the absence of the compound of formula (I)) would be produced by such analgesic opiate agent. The invention therefore contemplates the use of respiratory depression-combatting compounds which mediate analgesia themselves, as well as respiratory depression-combatting compounds which do not mediate analgesia.

In such combination of the opiate agent (or other respiratory depression-mediating compound), and the respiratory depression-combatting compound, the dosage of the opiate agent for inducing analgesia, and the dosage of the formula (I) compound for reducing, treating or preventing respiratory depression, can be independently determined. The separate control of dosages for these two functions provides for greater flexibility in treating individual patients. This separate control is one of the advantages of the combination pharmaceutical compositions of the present invention.

The combination pharmaceutical compositions of the invention thus comprise a combination of (1) an effective amount of a therapeutic agent having a respiratory depression (side) effect, e.g., an opiate analgesic, and (2) an effective amount of a compound, e.g., a compound of formula (I) below, for reducing, treating or preventing respiratory depression.

Compounds of formula (I) are as follows:

| Compound | Delta Receptor $IC_{50}$ (nM) | Mouse Vas Deferens $ED_{50}$ (nM) |
|---|---|---|
| 1 | $2^a$ | 43 |
| 2 | $1^a$ | — |
| 3 | — | — |
| 4 | — | >1,000 |
| 5 | 1.6 | 260 |
| 6 | 4.0 | 25 |
| 7 | 1.1 | 560 |
| 8 | 0.86 | 30 |
| 9 | 1.5 | 450 |
| 10 | 1.1 | 90 |
| 11 | — | — |
| 12 | 1.2 | 250 |
| 13 | 0.3 | 200 |
| 14 | 2 | $pA_2 = 7.1^b$ |
| 15 | 2.8 | $pA_2 = 7.0^b$ |
| 16 | 3.1 | $pA_2 = 7.2^b$ |
| 17 | 1.5 | $pA_2 = 8.2^c$ |
| 18 | 1.3 | 250 |
| 19 | 2.6 | 37 |
| 20 | 1.3 | 78 |
| 21 | 1.6 | 44 |
| 22 | 0.7 | 4400 |
| 23 | 3.3 | 42 |
| 24 | 2.3 | 20 | wherein:

Ar is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent $R^1$, Y is selected from the group consisting of:

hydrogen;

halogen;

$C_1$–$C_6$ alkyl, $C_2$–$C_6$ alkenyl, $C_2$–$C_6$ alkynyl;

$C_1$–$C_6$ haloalkyl;

$C_1$–$C_6$ alkoxy;

$C_3$–$C_6$ cycloalkoxy;

sulfides of the formula $SR^8$ where $R^8$ is $C_1$–$C_6$ alkyl, $C_2$–$C_6$ alkenyl, $C_2$–$C_6$ alkynyl, $C_3$–$C_6$ cycloalkyl, arylalkyl having a $C_5$–$C_{10}$ aryl moiety and an $C_1$–$C_6$ alkyl moiety, or $C_5$–$C_{10}$ aryl;

sulfoxides of the formula $SOR^8$ where $R^8$ is the same as above;

sulfones of the formula $SO_2R^8$ where $R^8$ is the same as above;

nitrile;

$C_1$–$C_6$ acyl;

alkoxycarbonylamino (carbamoyl) of the formula $NHCO_2R^8$ where $R^8$ is the same as above;

carboxylic acid, or an ester, amide, or salt thereof;

aminomethyl of the formula $CH_2NR^9R^{10}$ where $R^9$ and $R^{10}$ may be the same or different, and may be hydrogen, $C_1$–$C_6$ alkyl, $C_2$–$C_6$ alkenyl, $C_2$–$C_6$ alkynyl, $C_2$–$C_6$ hydroxyalkyl, $C_2$–$C_6$ methoxyalkyl, $C_3$–$C_6$ cycloalkyl, or $C_5$–$C_{10}$ aryl, or $R^9$ and $R^{10}$ together may form a ring of 5 or 6 atoms, the ring atoms selected from the group consisting of N and C;

carboxamides of the formula $CONR^9R^{10}$ where $R^9$ and $R^{10}$ are the same as above, or $C_2$–$C_{30}$ peptide conjugates thereof; and sulfonamides of the formula $SO_2NR^9R^{10}$ where $R^9$ and $R^{10}$ are the same as above;

Z is selected from the group consisting of:

hydroxyl; and esters thereof;

hydroxymethyl, and esters thereof; and amino, and carboxamides and sulfonamides thereof;

G is carbon or nitrogen;

$R^1$ is hydrogen, halogen, or $C_1$–$C_4$ alkyl, $C_2$–$C_4$ alkenyl, $C_1$–$C_4$ alkynyl;

$R^2$ is hydrogen, halogen, or $C_1$–$C_4$ alkyl, $C_2$–$C_4$ alkenyl, $C_1$–$C_4$ alkynyl;

$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;

$R^6$ is selected from the group consisting of:

hydrogen;

$C_1$–$C_6$ alkyl, $C_2$–$C_6$ alkenyl, $C_2$–$C_6$ alkynyl;

$C_3$–$C_6$ cycloalkyl;

arylalkyl having $C_5$–$C_{10}$ aryl and $C_1$–$C_6$ alkyl moieties;

alkoxyalkyl having $C_1$–$C_4$ alkoxy and $C_1$–$C_4$ alkyl moieties;

$C_2$–$C_4$ cyanoalkyl;

$C_2$–$C_4$ hydroxyalkyl;

aminocarbonylalkyl having a $C_1$–$C_4$ alkyl moiety; and $R^{12}COR^{13}$, where $R^{12}$ is $C_1$–$C_4$ alkylene, and $R^{13}$ is $C_1$–$C_4$ alkyl or $C_1$–$C_4$ alkoxy; and $R^7$ is hydrogen or fluorine, or a pharmaceutically acceptable ester or salt thereof.

In preferred methods and pharmaceutical compositions of the present invention, the substituents of the compound of formula (I) for reducing, treating or preventing respiratory depression are as follows.

Preferably, Ar is a 6-member carbocyclic aromatic (benzene) ring and $R^1$ is hydrogen.

In certain preferred methods, Y is a carboxamide of the formula $CONR^9R^{10}$, and $R^9$ and $R^{10}$ preferably are the same or different and are each hydrogen, $C_1$ alkyl or $C_2$ alkyl, or together form a ring of five or six atoms, thereby forming a pyrrolidinyl or piperidino ring. In other preferred methods, Y is hydrogen or a sulfone of the formula $SO_2R^8$, and $R^8$ is preferably $C_1$–$C_6$ alkyl.

Furthermore, in preferred methods, G is N, $R^7$ and $R^2$ are each hydrogen, and Z is hydroxyl.

Preferably, $R^6$ is selected from the group consisting of hydrogen, $C_1$–$C_6$ alkyl, $C_2$–$C_6$ alkenyl and $C_2$–$C_6$ alkynyl, and more preferably, $R^6$ is selected from the group consisting of hydrogen, methyl, propyl, allyl and butenyl, and most preferably, $R^6$ is allyl.

In preferred methods, $R^3$, $R^4$ and $R^5$ are hydrogen or methyl, where the total number of methyl groups is one or two, and most preferably, $R^3$ and $R^5$ are both methyl, and $R^4$ is hydrogen.

Preferably, the compound for reducing, treating or preventing respiratory depression is selected from the group consisting of:

(−)-4-((αR)-α-((2R,SR)-4-allyl-2,5-dimethyl-1-piperazinyl)-3-hydroxybenzyl)-N,N-diethylbenzamide;

(−)-4-((αR)-α-((2R,5R-2,5-dimethyl-4-propyl-1-piperazinyl)-3-hydroxybenzyl)-N,N-diethylbenzamide;

4-((αR)-α-(2S,5S)-4-allyl-2,5-dimethyl-1-piperazinyl)-3-hydroxybenzyl)-benzamide;

(±)-3-((αR*)-α-((2S*,5R*)-4-allyl-2,5-dimethyl-1-piperazinyl)-3-hydroxybenzyl)benzamide;

N,N-diethyl-4-((αR)-3-hydroxy-α-((2R,5R)-2,5-dimethyl-1-piperazinyl)benzyl)benzamide;

4-((αR)-α-((2S,5S)-4-allyl-2,5-dimethyl-1-piperazinyl)-3-hydroxybenzyl)-N-ethyl-N-methylbenzamide;

3-((αR)-α-((2S,5S)-4-allyl-2,5-dimethyl-1-piperazinyl)benzyl)phenol;

3-((αS)-α-((2S,5S)-4-allyl-2,5-dimethyl-1-piperazinyl)benzyl)phenol;

(±)-N,N-diethyl-4-((αR*)-3-hydroxy-α-((2R*,5S*)-2,4,5-trimethyl-1-piporazinyl)benzyl)benzamide;

(+)-4-((αS)-α-((2S,5S)-4-allyl-2,5-dimethyl-1-piperazinyl)-3-hydroxybenzyl)-N,N-diethylbenzamide;

3-((αR)-4-(piperidinocarbonyl)-α-((2S,5S)-2,4,5-trimethyl-1-piperazinyl)benzyl)phenol;

3-((αR)-4-(1-pyrrolidinylcarbonyl)-α-((2S,5S)-2,4,5-trimethyl-1-piperazinyl)benzyl)phenol;

(±)-3-((αR*)-α-((2R*,5S*)-4-allyl-2,5-dimethyl-1-piperazinyl)-4-(methylsulfonyl)benzyl)phenol;

(±)-4-((αR*)-α-((2R*,5S*)-4-allyl-2,5-dimethyl-1-piperazinyl)-3-hydroxybenzyl)-N,N-dimethylbenzenesulfonamide (and, independently, each of the component isomers thereof);

(±)-3-((αR*)-α-((2S*,5R*)-4-allyl-2,5-dimethyl-1-piperazinyl)benzyl)phenol;

(±)-4-((αR*)-α-((2S*,5R*)-4-allyl-2,5-dimethyl-1-piperazinyl)-3-hydroxybenzyl)benzamide;

(±)-4-((αR*)-α-((2R*,5S*)-2,5-dimethyl-1-piperazinyl)-3-hydroxybenzyl)-N,N-diethylbenzamide;

(±)-cis-4-(α-(4-allyl-3,5-dimethyl-1-piperazinyl)-3-hydroxybenzyl)-N,N-diethylbenzamide;

cis-4-(α-(3,5-dimethyl-4-(methylallyl)-1-piperazinyl)-3-hydroxybenzyl)-N,N-diethyl-benzamide;

and pharmaceutically acceptable salts thereof.

Most preferably, the compound is (−)-4-((αR)-α-((2R,5R)-4-allyl-2,5-dimethyl-1-piperazinyl)-3-hydroxybenzyl)-N,N-diethylbenzamide;

(±)-4-((αR*)-α-((2S*,5R*)-4-allyl-2,5-dimethyl-1-piperazinyl)-3-hydroxybenzyl)-N,N-dimethylbenzenesulfonamide;

(+)-4-((αR)-α-((2R,5S)-4-allyl-2,5-dimethyl-1-piperazinyl)-3-hydroxybenzyl)-N,N-dimethylbenzenesulfon-amide; or (−)-4-((αR)-α-((2R,5S)-4-allyl-2,5-dimethyl-1-piperazinyl)-3-hydroxybenzyl)-N,N-dimethylbenzenesulfonamide, or a pharmaceutically acceptable salt thereof.

In addition to methods of treating, reducing or preventing respiratory depression, the present invention also provides methods for screening and characterizing respiratory depression-suppressing compounds, comprising conducting activity reversal assays of candidate respiratory depression-suppressing compounds which in receptor tissue transductionally mediate a respiratory depression effect in response to a respiration-depressing composition.

The activity reversal assays are conducted comparatively, in the absence and in the presence of an anti-suppression compound of formula (I), to determine if the (respiratory depression) suppressing activity of the candidate compound is markedly reversed in the receptor system by the presence of the anti-suppression compound of formula (I). If so, the assay indicates the candidate respiratory depression-suppressing compound as possessing potential bioefficacy for supressing respiratory depression effects incident to the use of other therapeutic agents.

Preferred anti-suppression compounds of formula (I) which may be usefully employed in the above-discussed screen assay include:

(−)-4-((αS)-α-((2R,5R)-4-allyl-2,5-dimethyl-1-piperazinyl)-3-hydroxybenzyl)-N,N-diethylbenzamide;
(−)-4-((αS)-α-((2R,5R)-2,5-dimethyl-4-propyl-1-piperazinyl)-3-hydroxybenzyl)-N,N-diethylbenzamide;
cis-4-(α-(4-((Z)-2-butenyl)-3,5-dimethyl-1-piperazinyl)-3-hydroxybenzyl)-N,N-diethylbenzamide; and acceptable salts thereof.

Additionally, the present invention provides the following preferred compounds of formula (I), which can be included, for example, in a pharmaceutical composition containing the compound and a pharmaceutically acceptable carrier.

These pharmaceutical compositions can be used, for example, in a form suitable for injectable or spinal administration. The above-referenced preferred compounds are as follows:

(−)-4-((αR)-α-((2R,SR)-4-allyl-2,5-dimethyl-1-piperazinyl)-3-hydroxybenzyl)-N,N-diethylbenzamide;
(−)-4-((αR)-α-((2R,5R)-2,5-dimethyl-4-propyl-1-piperazinyl)-3-hydroxybenzyl)-N,N-diethylbenzamide;
4-((αR)-α-(2S,5S)-4-allyl-2,5-dimethyl-1-piperazinyl)-3-hydroxybenzyl)-benzamide;
(±)-3-((αR*)-α-((2S*,5R*)-4-allyl-2,5-dimethyl-1-piperazinyl)-3-hydroxybenzyl)benzamide;
N,N-diethyl-4-((αR)-3-hydroxy-α-((2R,5R)-2,5-dimethyl-1-piperazinyl)benzyl)benzamide;
4-((αR)-α-((2S,5S)-4-allyl-2,5-dimethyl-1-piperazinyl)-3-hydroxybenzyl)-N-ethyl-N-methylbenzamide;
3-((αR)-α-((2S,5S)-4-allyl-2,5-dimethyl-1-piperazinyl)benzyl)phenol;
(±)-N,N-diethyl-4-((αR*)-3-hydroxy-α-((2R*,5S*)-2,4,5-trimethyl-1-piperazinyl)benzyl)benzamide;
(±)-4-((αR*)-α-((2R*,5S*)-4-allyl-2,5-dimethyl-1-piperazinyl)-3-hydroxybenzyl)-N,N-dimethylbenzenesulfonamide;
(+)-4-(((αR)-α-((2R,5S)-4-allyl-2,5-dimethyl-1-piperazinyl)-3-hydroxybenzyl)-N,N-dimethylbenzenesulfon-amide;
(−)-4-((αR)-α-((2R,5S)-4-allyl-2,5-dimethyl-1-piperazinyl)-3-hydroxybenzyl)-N,N-dimethylbenzenesulfonamide,
(+)-4-((αS)-α-((2S,5S)-4-allyl-2,5-dimethyl-1-piperazinyl)-3-hydroxybenzyl)-N,N-diethylbenzamide; and pharmaceutically acceptable salts thereof.

These preferred compounds of the invention have utility in medical therapy, in particular for reducing, treating or preventing respiratory depression associated with respiratory depression-mediating drugs, including certain analgesics such as mu opiate analgesics.

The respiratory depression-combatting compositions of the present invention may be formulated with the respiratory depression-mediating agent, as a unitary composition. Alternatively, the respiratory depression-combatting compositions of the present invention may be separately, independently administered to a patient in need of same, to combat the respiratory depression effects otherwise obtaining in use of the respiratory depression-mediating agent, e.g., a respiratory depressant such as morphine, fentanyl or the like. The invention contemplates the use of any means and/or of modality of administration of the respiratory depression-combatting compositions of the invention, in conjunction with the drug or bioactive agent mediating the respiratory depression.

Compounds of the above general formula (I) exhibit binding selectivity for receptor(s). Depending on the structure and stereo-specificity of the particular formula (I) compounds, such compounds may exhibit binding ability to receptor(s) selected from the group consisting of delta receptors, mu receptors, kappa receptors, sigma receptors, and combinations of such receptors.

Various compounds within general formula (I) exhibit delta receptor agonist activity including reducing, treating or preventing respiratory depression. Other compounds of formula (I) exhibit delta receptor antagonist activity which are useful as agonist conjugates for assay applications, for example, to identify agonist species. Still other compounds within the general formula exhibit mu receptor activity, and more particularly, in some instances, mixed mu receptor/delta receptor activity.

In the case of delta receptor agonists, activity is generally distinguished and measured by activity in the electrically stimulated mouse vas deferens assay. Further, empirical determinations utilizing compounds of the present invention provide strong evidence of the existence of a delta receptor subtype in the brain that is different from the delta receptor in the mouse vas deferens.

In consequence of the existence of such delta receptor subtypes, other receptor binding assays or screening techniques may be employed as a further predictor of agonist or antagonist activity for specific compounds of the present invention.

The compounds used in the methods and pharmaceutical compositions of the present invention preferably have the following in vitro profile according to the delta receptor $IC_{50}$ and mouse vas deferens $ED_{50}$ tests described in Example 12. Preferably, the $IC_{50}$ is between about 0.01 and about 100 nM; more preferably, the $IC_{50}$ is less than about 100 nM; even more preferably, the $IC_{50}$ is less than about 10 nM; even more preferably, the $IC_{50}$ is less than about 2 nM, and most preferably, the $IC_{50}$ is less than about 1 nM. Preferably, the mouse vas deferens $ED_{50}$ is as high as possible; preferably, greater than about 10 nM; more preferably, greater than about 30 nM; even more preferably, greater than about 50 nM; and most preferably, greater than about 100 nM.

In general, it is preferred to have a ratio of $IC_{50}:ED_{50}$ of about 1:10; and more preferably, about 1:100.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethyl piperazine compound for its intended utility (examples of substituents for substituted alkyl groups include halogen (e.g., fluoro, chloro, bromo, and iodo), amino, amido, $C_1$–$C_4$ alkyl, $C_1$–$C_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethyl piperazine compound for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethyl piperazine compound for its intended utility. Examples of substituents for substituted aryl groups include one or more of halogen (e.g., fluoro, chloro, bromo, and iodo), amino, amido, $C_1-C_4$ alkyl, $C_1-C_4$ alkoxy, nitro, trifluoromethyl, hydroxy, hydroxyalkyl containing a $C_1-C_4$ alkyl moiety, etc.

The compounds contemplated by the invention include those of formula (I) per se, as well as physiologically functional derivatives thereof.

By "physiologically functional derivative" is meant a pharmaceutically acceptable salt, ether, ester or salt of an ether or ester of the compound of formula (I) or any other compound which, upon administration to the recipient, is capable of providing (directly or indirectly) the said compound of formula (I) or an active metabolite or residue thereof. Phenolic $C_1-C_6$ alkyl ethers are a sub-class of physiologically functional derivatives of the compounds of formula (I).

In enantiomeric forms, compounds of the invention include individual enantiomers of the compounds of formula (I) in single species form substantially free of the corresponding enantiomer, as well as in admixture (in mixtures of enantiomeric pairs and/or in mixtures of multiple enantiomer species).

A sub-class of compounds within the scope of formula (I) are the pharmaceutically acceptable esters and salts thereof.

Examples of pharmaceutically acceptable esters of the invention include carboxylic acid esters of hydroxy groups in compounds of formula (I) in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl) aminocarbonyl); and inorganic esters (e.g. mono-, di- or triphosphate).

Examples of pharmaceutically acceptable salts of the compounds of formula (I) and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_1-C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxy group consist of the anion of said compound in combination with a suitable cation such as Na+, $NH_4^+$ or $NX_4^+$ (wherein X is for example a $C_{1-4}$ alkyl group).

For therapeutic use, salts of compounds of formula (I) will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

As used herein, in reference to the present invention, the term "hydrocarbyl" is intended to encompass a group containing only carbon and hydrogen atoms, which may contain double or triple bonds and which may be cyclic or aromatic in nature.

The compounds of the invention when used in pharmaceutical or diagnostic applications desirably are prepared in substantially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered compounds of formula (I) at any suitable therapeutically effective and safe dosage, as may readily be determined within the skill of the art, and without undue experimentation.

In in vitro tests for agonist/antagonist activity, such as receptor binding affinity tests, and inhibition of electrically stimulated muscle twitch tests, compounds of the present invention exhibit potency over a range of from nanomolar to micromolar concentrations, depending on the specific compound employed.

In general, while the effective dosage of compounds of the invention for therapeutic use may be widely varied in the broad practice of the invention, depending on the specific application, condition, or disease state involved, as readily determinable within the skill of the art, suitable therapeutic doses of the formula (I) compounds, for each of the appertaining compositions described herein, and for achievement of therapeutic benefit in treatment of each of the conditions described herein, will be in the range of 10 micrograms ($\mu$g) to 100 milligrams (mg) per kilogram body weight of the recipient per day, preferably in the range of 50 $\mu$g to 75 mg per kilogram body weight per day, and most preferably in the range of 100 $\mu$g to 50 mg per kilogram body weight per day. The desired dose is preferably presented as two, three, four, five, six, or more sub-doses administered at appropriate intervals throughout the day. These sub-doses may be administered in unit dosage forms, for example, containing from 10 $\mu$g to 1000 mg, preferably from 50 $\mu$g to 500 mg, more preferably from 50 $\mu$g to 250 mg, and most preferably from 50 $\mu$g to 10 mg of active ingredient per unit dosage form. Alternatively, if the condition of the recipient so requires, the doses may be administered as a continuous infusion.

The mode of administration and dosage forms will of course affect the therapeutic amounts of the compounds which are desirable and efficacious for the given treatment application.

For example, orally administered dosages typically are at least twice, e.g., 2–10 times, the dosage levels used in parenteral administration methods, for the same active ingredient. In oral administration, dosage levels for delta receptor binding compounds of the invention may be on the order of 5–200 mg/70 kg body weight/day. In tablet dosage forms, typical active agent dose levels are on the order of 10–100 mg per tablet.

The compounds of formula (I) may be administered per se as well as in the form of pharmaceutically acceptable ethers, esters, salts, and other physiologically functional derivatives thereof.

The present invention also contemplates pharmaceutical formulations, both for veterinary and for human medical use, which comprise as the active agent one or more compound(s) of the invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formuations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The compounds of formula (I) and pharmaceutically acceptable esters, salts, and other physiologically functional derivatives thereof, may be formed by the exemplary synthetic techniques described in the aforementioned International Publication No. WO93/15062.

The respiratory depression-combatting compositions of the present invention may also advantageously attenuate side effects of drug agents other than respiratory depression.

For example, fentanyl also reduces muscle rigidity through mu receptor activation. Such fentanyl-induced muscle rigidity can be inhibited by a delta agonist compound such as (±)-4-((αR*)-α-((2S*,5R*)-4-allyl-2,5-dimethyl-1-piperazinyl)-3-hydroxybenzyl)-N,N-diethylbenzamide.

Moreover, such combination of mu agonist and delta agonist compounds are synergistic, in selectively antagonizing each other's adverse side effects. The compound (±)-4-((αR*)-α-((2S*,5R*)-4-allyl-2,5-dimethyl-1-piperazinyl)-3-hydroxybenzyl)-N,N-diethylbenzamide at high dosages may induce seizure activity via delta receptor activation. The mu agonist fentanyl, for example, has been shown to antagonize such high dose seizure effect, while the delta agonist antagonizes the respiratory depression and muscle rigidity side effects of fentanyl. At the same time, the combination of such agonist compounds results in an additive analgesic effect.

The nausea/vomiting effects of mu-opioid analgesics may also be attenuated by the delta opioid agonist. The combination of mu- and delta-opioid agonists or compounds possessing both mu- and delta-opioid receptor activity may produce less nausea and vomiting as compared to currently used mu-opioid analgesics.

The invention is further illustrated by the following non-limiting examples.

Certain specifications and methods common to many of the following examples relating to chemical synthesis are described in the next paragraph.

Melting points were determined with a Thomas-Hoover apparatus and are uncorrected. All chemical reagents were purchased from Aldrich Chemical Company, Milwaukee, Wis., unless otherwise specified. Commercial solvents were used without further purification except tetrahydrofuran, which was distilled from potassium metal. Nuclear magnetic resonance (NMR) spectra were variously obtained with Perkin-Elmer R-24, Varian XL-200, or XL-300 spectrometers. HPLC analyses were performed with a Waters liquid chromatography system equipped with a 700 Satellite WISP, 600E System Controller and a 991 Photodiode Array detector, with either a Cyclobond I column (4.6×250 mm, Advanced Separations Technologies, Whippany, N.J.) or a μ-Bondapak C-18 column (125 Å, 3.9×300 mm, Waters Chromatography Division, Millipore Corporation, Milford, Mass.) at a flow rate of 1 ml/min. Analytical gas chromatography was performed on a Hewlett-Packard Series II instrument, Model 5890 with flame ionization detector using helium as the carrier gas (injector temperature, 225° C.; detector temperature, 250° C.). Optical rotations were obtained with a Perkin-Elmer 241 polarimeter. Mass spectra were performed by Oneida Research Services, Whitesboro, N.Y. X-Ray crystallography was performed by Molecular Structure Corporation, College Station, Tex. Analytical thin layer chromatography was performed on Analtech glass plates pre-coated with silica gel GF (250 microns), and preparative thin layer chromatography on Analtech Uniplates pre-coated with silica gel GF (1000 and 2000 microns). Elemental analyses were performed by Atlantic Microlab, Norcross, Ga.

EXAMPLE 1

(−)-4-(αR)-α-((2R,SR)-4-Allyl-2,5-dimethyl-1-piperazinyl)-3-hydroxybenzyl)-N,N-diethylbenzamide A mixture of 4-carboxybenzaldehyde (100 g, 0.66 mol), 1L of dimethylformamide and 2L of dichloromethane was cooled in an ice bath. Thionyl chloride (53 mL, 0.73 mol) was added dropwise while stirring. After 18 hours at room temperature, the mixture was cooled again and diethylamine (275 mL, 2.6 mol) was added dropwise. After stirring at room temperature for one hour the solvent was evaporated, and the residue was dissolved in aqueous 0.1 M sodium hydroxide and extracted with ethyl acetate. The organic layers were washed with water and brine, dried over sodium sulfate and evaporated to give a yellow oil. Chromatography on silica gel with ethanol (0–2%) in dichloromethane gave 44.2 g (32%) of 4-formyl-N,N-diethylbenzamide as a yellow oil.

A solution of 3-bromophenol (500 g, 2.89 mol), tert-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined ether extracts were dried over sodium sulfate and the solvent removed to give 846 g of 3-(bromophenoxy)-tert-butyldimethylsilane as a pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-(Bromophenoxy)-tert-butyldimethylsilane (61.7 g, 0.21 mol) was dissolved in 500 mL of dry tetrahydrofuran under nitrogen and cooled to −78° C. A solution of 1.6 M n-butyllithium in hexane (132 mL, 0.21 mol) was added dropwise at a rate to maintain the temperature below −70° C. The reaction was stirred for thirty minutes after the addition was complete and the cold solution was transferred via cannula to another vessel containing a cold (−78° C.) solution of 4-formyl-N,N-diethylbenzamide (44.1 g, 0.21 mol), from above, in 500 mL of dry tetrahydrofuran under nitrogen. The transfer rate was monitored to maintain the temperature below −70° C. After stirring for one hour at −78° C., the reaction was quenched with saturated aqueous ammonium chloride, warmed to room temperature and diluted with diethyl ether. The ether layer was washed with water and brine, dried over sodium sulfate and evaporated to give a yellow oil. Chromatography on silica gel with ethanol (0–1%) in dichloromethane gave 45.4 g (52%) of 4-(3-(tert-butyldimethylsilyloxy)-α-hydroxybenzyl)-N,N-diethylbenzamide as a white solid.

NMR (200 MHz, CDCl$_3$) δ: 0.15 (s, 6H); 1.0 (s, 9H); 1.2 (br m, 6H); 2.8 (br s, 1H); 3.25 (br m, 2H); 3.5 (br m, 2H); 5.75 (s, 1H); 6.75 (d, J=8 Hz, 1H); 6.85 (s, 1H); 7.95 (d, J=8 Hz, 1H); 7.2 (t, J=8 Hz, 1H); 7.35 (AB q, J=8 Hz, 4H).

Thionyl chloride (5.3 mL, 0.075 mol) was added to a solution of the benzhydryl alcohol from above (19.75 g, 0.048 mol) in 350 mL of dichloromethane. After stirring at room temperature overnight the solvent was evaporated, the residue was redissolved in toluene and again evaporated to drive off excess thionyl chloride and afford crude 4-(3-(tert-butyldimethylsilyloxy)-α-chlorobenzyl)-N,N-diethylbenzamide.

The crude benzhydryl chloride (approximately 0.047 mol), (2R,SR)-2,5-dimethylpiperazine (6.0 g, 0.53 mol), prepared from L-Ala-L-Ala-diketopiperazine (Bachem Chemicals, Philadelphia, Pa.) as described in *J. Org. Chem.* 50: 4909–13 (1985), sodium iodide (9.0 g, 0.06 mol), and disopropylethylamine (14.19 g, 0.11 mol) were heated to reflux in acetonitrile (300 mL) under nitrogen for four hours. The acetonitrile was evaporated. The residue was dissolved in ethyl acetate (0.5 L) and washed with water. The organic phase was dried over sodium sulfate and concentrated in vacuo. The residue was dissolved in dichloromethane and purified on a short column of silica gel with ethanol (5%) in dichloromethane to provide a 1:1 mixture of two benzhydrylpiperazine diastereomers.

The mixture of benzhydrylpiperazine epimers (7.6 g, 14.9 mmol) was dissolved in 50 mL of dry tetrahydrofuran with 1.6 mL (18.6 mmol) of allyl bromide and 5.1 g (36.9 mmol) of sodium carbonate and stirred at room temperature under nitrogen for 2 days. The reaction solution was poured into ice water/ethyl acetate and separated. The organic layer was dried over sodium sulfate, and concentrated in vacuo. The residue was dissolved in a small amount of dichloromethane and placed on a column of silica gel. The diastereomers were separated by elution with a stepwise gradient of ethanol in dichloromethane. The first isomer was eluted with 1.3% ethanol in dichloromethane, and the second isomer was obtained with 1.6% ethanol in dichloromethane. Fractions containing the second isomer were combined and the solvent removed in vacuo to give 1.44 g of 4-(αR)-α-((2R,5R)-4-allyl-2,5-dimethyl-1-piperazinyl)-3-(tert-butyldimethylsilyloxy)benzyl)-N,N-diethylbenzamide as a brown oil.

NMR (300 MHz, DMSO-$d_6$): δ 0.12 (s, 6H); 0.89 (m, 12H); 0.93 (d, J=6.5 Hz, 3H); 1.05 (br s, 6H); 2.13 (app t, J=10.4 Hz, 1H); 2.25–2.37 (m, 3H); 2.55 (dd, partially obscured by DMSO, 1H); 2.71 (dd, J1=8.2 Hz, J2=14.2 Hz, 1H); 2.82 (br d, J=6.2 Hz, 1H); 3.12 (br s, 2H); 3.19 (m, obscured by water, 1H); 3.36 (br S, 2H); 4.55 (s, 1H); 5.08 (d, J=10.8 Hz, 1H), 5.14 (d, J=21.5 Hz, 1H); 5.72–5.83 (m, 1H); 6.62 (d, J=8.7 Hz, 1H); 6.99 (s, 1H); 7.00 (d, J=8.1 Hz, 1H); 7.12 (t, J=7.9 Hz, 1H); 7.23 (d, J=8.2 Hz, 2H); 7.33 (d, J=8.2 Hz, 2H).

The brown oil (1.05 g, 1.9 mmol) was dissolved in 8 mL of acetonitrile with 0.53 g (2.9 mmol) of tetraethylammonium fluoride dihydrate and stirred for 30 minutes at room temperature. After evaporation of solvent, the residue was redissolved in 1N hydrochloric acid and diethyl ether. The aqueous phase was separated and neutralized to pH 8 with 1N sodium hydroxide solution. The product was extracted using dichloromethane and washed with brine. The organic phase was dried over sodium sulfate and the solvent removed to give 0.69 g of (−)-4-((αR)-α-((2R,5R)-4-allyl-2,5-dimethyl-1-piperazinyl)-3-hydroxybenzyl)-N,N-diethylbenzamide.

NMR (300 MHz, DMSO-$d_6$): δ 0.95 (d, J=5.4 Hz, 3H); 1.00 (d, J=5.4 Hz, 3H); 1.13 (br s, 6H); 2.19 (app t, J=10.0 Hz, 1H); 2.26–2.41 (m, 3H); 2.55 (m, partially obscured by DMSO, 1H); 2.81 (dd, J1=7.9 Hz, J2=14.1 Hz, 1H); 2.89 (br d, J=6.2 Hz, 1H); 3.21 (br s, 2H); 3.21 (m, obscured, 1H); 3.39 (br s, 2H); 4.54 (s, 1H); 5.17 (d, J=11.3 Hz, 1H), 5.22 (d, J=19.6 Hz, 1H); 5.82–5.96 (m, 1H); 6.60 (d, J=7.8 Hz, 1H); 6.93 (m, 2H); 7.11 (t, J=7.9 Hz, 1H); 7.31 (d, J=7.9 Hz, 2H); 7.52 (d, J=7.9 Hz, 2H); 9.39 (s, 1H).

Mass spectrum (CI-CH$_4$) m/z: 436 (M+1, 12%), 282 (100%), 153 (3%). $[\alpha]_D^{20}$=−27.8° (ethanol, c=1.2).

A portion of the free amine (0.100 g) was dissolved in ethanol and titrated with ethanolic hydrogen chloride to pH 4.0, followed by precipitation with diethyl ether from dichloromethane to give 0.089 g of the monohydrochloride salt as a hygroscopic beige powder. Calculations for $C_{27}H_{37}N_3O_2$ HCl 0.75 H$_2$O: C, 66.78; H, 8.20; N, 8.65; Cl, 7.30. Found: C, 66.90; H, 8.05; N, 8.69; Cl, 7.13.

EXAMPLE 2

(−)-4-((αS)-α-((2R,5R)-4-Allyl-2,5-dimethyl-1-piperazinyl)-3-hydroxybenzyl)-N,N-diethylbenzamide The first isomer to elute from the column of Example 1 was obtained as 1.39 g of a brown oil.

NMR (300 MHz, DMSO-$d_6$): δ 0.11 (s, 6H); 0.86 (d, J=6.8 Hz, 3H); 0.88 (m, 9H); 0.94 (d, J=6.8 Hz, 3H); 1.02 (br s, 6H); 2.14 (app t, J=10.7 Hz, 1H); 2.25–2.38 (m, 3H); 2.55 (dd, partially obscured by DMSO, 1H); 2.73 (dd, J1=7.4 Hz, J2=13.9 Hz, 1H); 2.84 (br s, 1H); 3.13 (br s, 2H); 3.28 (m, obscured by water, 1H); 3.34 (br s, 2H); 4.55 (s, 1H); 5.09 (d, J=11.3 Hz, 1H), 5.14 (d, J=19.9 Hz, 1H); 5.74–5.84 (m, 1H); 6.63 (d, J=7.8 Hz, 1H); 6.90 (s, 1H); 7.02 (d, J=7.6 Hz, 1H); 7.13 (t, J=7.8 Hz, 1H); 7.23 (d, J=8.1 Hz, 2H); 7.47 (d, J=8.1 Hz, 2H).

The brown oil (0.95 g, 1.73 mmol) was dissolved in 8 mL of acetonitrile with 0.48 g (2.6 mmol) of tetraethylammonium fluoride dihydrate and stirred for 30 minutes at room temperature. After evaporation of solvent, the residue was redissolved in 1N hydrochloric acid and diethyl ether. The aqueous phase was separated and neutralized to pH 8 with 1N sodium hydroxide solution. The product was extracted using dichloromethane, then washed with brine. The organic phase was dried over sodium sulfate and the solvent removed to give 0.64 g. of (−)-4-((αS)-α-((2R,5R)-4-allyl-2,5-dimethyl-1-piperazinyl)-3-hydroxybenzyl)-N,N-diethylbenzam-ide.

NMR (300 MHz, DMSO-$d_6$): δ 0.89 (d, J=5.8 Hz, 3H); 0.98 (d, J=5.8 Hz, 3H); 1.08 (br s, 6H); 2.10–2.43 (m, 4H); 2.56 (m, partially obscured by DMSO, 1H); 2.78 (dd, J1=7.7 Hz, J2=14.4 Hz, 1H); 2.97 (br d, J=6.0 Hz, 1H); 3.17–3.43 (m, 5H); 4.51 (s, 1H); 5.13 (d, J=8.6 Hz, 1H), 5.19 (d, J=15.6 Hz, 1H); 5.75–5.88 (m, 1H); 6.57 (d, J=6.8 Hz, 1H); 6.88 (m, 2H); 7.04 (t, J=7.7 Hz, 1H); 7.27 (d, J=8.0 Hz, 2H); 7.50 (d, J=8.0 Hz, 2H); 9.34 (s, 1H). Mass spectrum (CI-CH4) m/z: 436 (M+1, 23%), 282 (100%), 153 (4%). $[\alpha]_D^{20}$=−27.3° (ethanol, c=1.2).

A portion of the free amine (0.100 g) was dissolved in ethanol and titrated with ethanolic hydrogen chloride to pH 4.0, followed by precipitation with diethyl ether from dichloromethane to give 0.075 g of the monohydrochloride salt as a hygroscopic off-white powder. Calculations for $C_{27}H_{37}N_3O_2$ HCl 0.5 H$_2$O: C, 67.41; H, 8.17; N, 8.73; Cl, 7.37. Found: C, 67.16; H, 8.18; N, 8.81; Cl, 7.26.

EXAMPLE 3

(−)-4-((αR)-α-((2R,5R)-2,5-Dimethyl-4-propyl-1-piperazinyl)-3-hydroxybenzyl)-N,N-diethylbenzamide (−)-4-((αR)-α-((2R,5R-4-Allyl-2,5-dimethyl-1-piperazinyl)-3-hydroxybenzyl)-N,N-diethylbenzamide (0.075 g, 0.17 mmol, Example 1) was dissolved in toluene (10 mL), added to a 3-neck flask containing Lindlar's catalyst (0.071 g, ca. 0.033 mmol Pd) and stirred for 3.5 hours under a hydrogen atmosphere. The solution was filtered through celite, the solvent was evaporated under vacuum, and the residue was purified on silica gel with 5% ethanol in dichloromethane to give 0.065 g. of (−)-4-((αR)-α-((2R,5R)-2,5-dimethyl-4-propyl-1-piperazinyl)-3-hydroxybenzyl)-N,N-diethylbenzamide as a light-brown solid.

NMR (300 MHz, DMSO-$d_6$): δ 0.75–1.41 (m, 17H); 2.10–2.43 (m, 4H); 2.56 (m, partially obscured by DMSO, 1H); 2.87 (m, 1H); 3.03–3.52 (m, 6H); 4.50 (s, 1H); 6.57 (d, J=7.4 Hz, 1H); 6.91 (m, 2H); 7.07 (t, J=7.9 Hz, 1H); 7.27 (d, J=7.7 Hz, 2H); 7.48 (d, J=7.7 Hz, 2H); 9.33 (s, 1H). Mass spectrum (CI-CH4) n/z: 438 (M+1, 5%), 282 (100%), 155 (4%). $[\alpha]_D^{20}$=−37.5° (ethanol, c=1.2).

A portion of the free amine (0.055 g) was dissolved in ethanol and titrated with ethanolic hydrogen chloride to pH 4.0, followed by precipitation with diethyl ether from dichloromethane to give 0.045 g of the monohydrochloride salt as a hygroscopic beige powder. Calculations for $C_{27}H_{39}N_3O_2$ HCl 0.5 $H_2O$: C, 67.13; H, 8.55; N, 8.70. Found: C, 67.23; H, 8.55; N, 8.49.

EXAMPLE 4

(−)-4-((αS)-α-((2R,5R)-2,5-Dimethyl-4-propyl-1-piperazinyl)-3-hydroxybenzyl)-N,N-diethylbenzamide (−)-4-((αS)-α-((2R,5R)-4-Allyl-2,5-dimethyl-1-piperazinyl)-3-hydroxybenzyl)-N,N-diethylbenzamide (0.200 g, 0.46 mmol, Example 2) was dissolved in toluene (10 mL) and stirred for 4 hours under a hydrogen atmosphere. The solution was filtered through celite to give 0.182 g of crude product. The phenol was reprotected as follows to improve chromatographic resolution. A mixture of crude product (0.18 g), tert-butylchlorodimethylsilane (0.93 g), and imidazole (0.070 g) in 10 mL of acetonitrile was stirred overnight at room temperature. The reaction solution was poured into 100 mL of water and extracted with two 50 mL portions of dichloromethane. The combined extracts were dried over sodium sulfate and the solvent removed. The residue was purified on a column of silica gel with ethanol (0–4%) in dichloromethane to give 0.085 g of 4-((αS)-α-((2R,5R)-2,5-dimethyl-4-propyl-1-piperazinyl)-3(tert-butyldimethylsilyloxy)benzyl)-N,N-diethylbenzamide as a light-brown solid.

The material (0.080 g) was dissolved in acetonitrile (5 mL) and treated with tetraethylammonium fluoride dihydrate (0.040 g). After 30 minutes the solvent was removed under reduced pressure. The residue was dissolved in 1N hydrochloric acid (5 mL) and washed two times with diethyl ether. The aqueous phase was then adjusted to pH 9 with 1N sodium hydroxide solution and extracted with dichloromethane. The dichloromethane extracts were combined, dried over sodium sulfate, and the solvent removed under reduced pressure to give 0.056 g of (−)-4-((αS)-α-((2R,5R)-2,5-dimethyl-4-propyl-1-piperazinyl)-3-hydroxybenzyl)-N,N-diethylbenzamide as a light-brown solid.

NMR (300 MHz, DMSO-$d_6$): δ 0.72–1.41 (m, 17H); 1.95–2.34 (m, 4H); 2.56 (m, partially obscured by DMSO, 1H); 2.91 (m, 1H); 3.02–3.48 (m, 6H); 4.47 (s, 1H); 6.56 (br s, 1H); 6.83 (m, 2H); 7.05 (m, 1H); 7.24 (d, J=6.5 Hz, 2H); 7.46 (d, J=6.5 Hz, 2H); 9.31 (s, 1H). Mass spectrum (CI-CH4) m/z: 438 (M+1, 12%), 282 (100%), 155 (4%). $[α]_D^{20}$=−36.7° (ethanol, c=1.3).

The free amine (0.044 g) was dissolved in ethanol and titrated with ethanolic hydrogen chloride to pH 4.0, followed by precipitation with diethyl ether from dichloromethane to give 0.031 g of the monohydrochloride salt as a hygroscopic off-white powder. Calculations for $C_{27}H_{39}N_3O_2$ HCl $H_2O$: C, 65.90; H, 8.60; N, 8.54. Found: C, 65.72; H, 8.41; N, 8.52.

EXAMPLE 5

4-((αR)-α-(2S,5S)-4-Allyl-2,5-dimethyl-1-piperazinyl)-3-hydroxybenzyl)-benzamide 3-(Bromophenoxy)-tert-butyldimethylsilane (146 g, 0.51 mol, Example 1, infra) was dissolved in dry tetrahydrofuran under nitrogen and cooled to −78° C. A solution of 1.6 M n-butyllithium in hexane (318 mL, 0.51 mol) was added dropwise at a rate to maintain temperature below −70° C. The reaction was stirred for 30 minutes after the addition was complete, and the cold solution was transferred to another vessel containing a cold (−78° C.) solution of 4-bromobenzaldehyde (94.3 g, 0.51 mol) in 1000 mL of dry tetrahydrofuran under nitrogen. The transfer rate was monitored to maintain reaction temperature below −70° C. The reaction mixture was stirred for another 45 minutes at −78° C. and then quenched with 100 mL of saturated aqueous ammonium chloride. After warming to room temperature, the mixture was diluted with 2000 mL of diethyl ether and washed with 2000 mL of water followed by 500 mL of saturated sodium chloride. The ethereal solution was dried over sodium sulfate and the solvent removed to give 197.2 g of crude α-(4-bromophenyl)-3-(tert-butyldimethylsilyloxy)benzyl alcohol as a yellow oil.

NMR (200 MHz, CDCl$_3$): δ 0.2 (s, 6H); 0.9 (s, 6H); 5.7 (s, 1H); 6.75 (dd, J1=2 Hz, J2=8 Hz, 1H); 6.8 (br s, 1H); 6.9 (d, J=8 Hz, 1H); 7.15 (t, J=8 Hz, 1H); 7.25 and 7.45 (AB q, J=8 Hz, 4H).

The crude benzhydryl alcohol (53.2 g, 135 mmol) was dissolved in 1000 mL of dichloromethane and 14.7 mL (202 mmol) of thionyl chloride was added dropwise. The solution was stirred overnight at room temperature and the solvent was removed under vacuum. The crude product was redissolved in 500 mL of toluene and the solvent again was removed under vacuum to eliminate excess thionyl chloride, providing crude α-(4-bromophenyl)-3-(tert-butyldimethylsilyloxy)benzyl chloride as a dark oil. NMR (200 MHz, CDCl$_3$): δ 0.2 (s, 6H); 1.0 (s, 9H); 6.0 (s, 1H); 6.78 (dd, J1=1 Hz, J2–8 Hz, 1H); 6.9 (m, 2H); 7.2 (t, J=8 Hz, 2H); 7.27 and 7.47 (AB q, J=8 Hz, 4H).

The crude benzhydryl chloride (approx. 42 mmol) was combined with 9.55 g (84 mmol) of (+)-(2S,5S)-2,5-dimethylpiperazine, prepared from L-Ala-L-Ala-diketopiperazine (Bachem Chemicals, Philadelphia, Pa.) as described in *J. Org. Chem.* 50: 4909–13 (1985), and 30 mL of toluene and heated at reflux overnight under nitrogen. The toluene was removed under vacuum, and the residue was redissolved in diethyl ether and washed with 1.0 M sodium hydroxide followed by saturated aqueous sodium chloride. The ether solution was dried over sodium sulfate and the solvent removed to give a dark oil. The product was purified by chromatography on silica gel (Waters Prep 500) with 0.5–0.7% ethanol in dichloromethane with 0.1% triethylamine to give 8.01 g (39%) of (2S,5S)-1-(4-bromo-α-(3-(tert-butyldimethylsilyloxy)phenyl)benzyl)-2,5-dimethylpiperazine as a 1:1 mixture of diastereomers.

The purified benzhydrylpiperazine (1.51 g, 3.1 mmol) was dissolved in 20 mL of dry tetrahydrofuran with 0.27 mL (3.2 mmol) of allyl bromide and 1.6 g (15.5 mmol) of sodium carbonate and heated at reflux overnight under nitrogen. The cooled reaction solution was filtered and the solvent removed to give 1.62 g of crude (2S,5S)-1-allyl-4-(4-bromo-α-(3-(tert-butyldimethylsilyloxy)phenyl)benzyl)-2,5-dimethylpiperazine as a yellow oil.

NMR (200 MHz, CDCl$_3$): δ 0.15 (s, 6H); 0.95–1.1 (m, 12H); 1.45 (m, 1H); 2.2–2.55 (m, 4H); 2.6 (m, 1H); 2.75–3.1 (m, 2H); 3.4 (m, 1H); 4.45 (s, 1H); 5.1–5.25 (m, 3H); 5.85 (m, 1H); 6.75 (d, J=8 Hz, 1H); 6.8–6.95 (m, 2H); 7.1 (m, 1H); 7.2–7.5 (m, 4H).

The product from above (1.40 g, 2.6 mmol) was dissolved in 10 mL of dry tetrahydrofuran and cooled to −78° C. under nitrogen. A solution of 1.6 M n-butyllithium in hexane (1.6 mL, 2.6 mmol) was added dropwise at a rate to maintain temperature below −70° C. After the orange solution was stirred an additional 30 minutes at low temperature, anhydrous carbon dioxide gas was introduced into the reaction solution at a rate to maintain temperature 30 below −60° C. Carbon dioxide addition was stopped when the color of the reaction solution became a pale yellow. The reaction was allowed to warm to room temperature with stirring and the solvent was removed under vacuum. The residue was redissolved in 50 mL of toluene and the solvent again removed under vacuum in order to eliminate residual n-bromobutane. The reaction provided 1.39 g of the lithium salt of 4-((αR)-α-((2S,5S)-4-allyl-2,5-dimethyl-1-piperazinyl)-3-(tert-butyldimethylsilyloxy)benzyl)benzoic acid.

The lithium benzoate salt (1.39 g, 2.8 mmol) was dissolved in dichloromethane and cooled to 0° C. Thionyl chloride (0.3 mL, 4.2 mmol) was added dropwise. After stirring for two hours at 0° C. concentrated ammonium hydroxide (6.0 mL) was added. The resulting dark yellow slurry was allowed to warm to room temperature and stirred for another hour. The reaction solution was washed with water and dried over sodium sulfate. After removal of the solvent, the residue was purified by chromatography on silica gel with 1–3% methanol in dichloromethane to give 0.10 g of 4-((αR)-α-((2S,5S)-4-allyl-2,5-dimethyl-1-piperazinyl)-3-(tert-butyldimethylsilyloxy)benzyl)benzamide as a yellow resin.

NMR (200 MHz, $CDCl_3$): δ 0.15 (s, 6H); 0.95 (s, 9H); 0.97 (d, J=6 Hz, 3H); 1.05 (d, J=6 Hz, 3H); 2.2–2.5 (m, 4H); 2.65 (m, 1H); 2.8 (m, 1H); 3.0 (m, 1H); 3.5 (m, 1H); 4.55 (s, 1H); 5.1 (d, J=10 Hz, 1H); 5.2 (d, J=16 Hz, 1H); 5.85 (m, 1H); 6.1 (br s, 2H); 6.65 (d, J=8 Hz, 1H); 6.9 (s, 1H); 6.95 (d, J=8 Hz, 1H); 7.1 (t, J=8 Hz, 1H); 7.55 and 7.7 (AB q, J=8 Hz, 4H).

The benzamide from above (0.10 g, 0.20 mmol) was dissolved in 2 mL of acetonitrile with 60 mg (0.3 mmol) of tetraethylammonium fluoride hydrate and stirred for 1 hour at room temperature. After evaporation of the solvent, the residue was redissolved in dichloromethane and washed with water (pH=8), then dried over sodium sulfate and the solvent removed to give 90 mg of a beige solid. The monohydrochloride salt was prepared by titration to pH 4.3 with ethanolic hydrogen chloride (approximately 0.2 M) followed by precipitation with diethyl ether to give 49 mg of 4-((αR)-α-((2S,5R)-4-allyl-2,5-dimethyl-1-piperazinyl)-3-hydroxybenzyl)benzamide hydrochloride as a hygroscopic white powder. Calculations for $C_{23}H_{29}N_3O_2$ HCl 1.5 $H_2O$: C, 62.36; H, 7.51; N, 9.49; Cl, 8.00. Found: C, 62.38; H, 7.42; N, 9.41; Cl, 8.10. Mass spec (CI-CH4): m/z 380 (M+1, 100%).

EXAMPLE 6

(±)-3-((αR*)-α-((2S*,5R*)-4-Allyl-2,5-dimethyl-1-piperazinyl)-3-hydroxybenzyl)-benzamide A 12 L, 3-necked round bottom flask was charged with trans-2,5-dimethylpiperazine (767 g, 6.72 mol), which had been recrystallized from toluene to mp=115–119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise at a rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0, The organic solvents were removed by distillation under vacuum. The remaining aqueous solution was washed with 1500 mL of ethyl acetate to remove any bis-carbamate impurity. The ethyl acetate wash was extracted with two 500 mL portions of 1 M hydrochloric acid to recover desired product. The acid extracts were combined with the original aqueous solution and the pH was adjusted to 11 by addition of 10 M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1 M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5–1 hour of heating. The reaction was cooled below reflux temperature and 2000 mL of toluene was carefully added. Ethanol was removed by azeotropic distillation at 105° C., while adding an additional 4000 mL of toluene to the reaction flask during the course of the distillation. After collection of 9000 mL of distillate, the reaction was cooled to 100° C. and 1000 mL of toluene was carefully added. The solution was slowly cooled to 5° C. and maintained at 5° C. for 30 minutes. The solution was filtered, washing the filter cake with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid.

3-(Bromophenoxy)-tert-butyldimethylsilane (155.2 g, 0.54 mol, Example 1, infra) was dissolved in 600 mL of dry tetrahydrofuran, dried further over molecular sieves, then transferred to a reaction flask and diluted to 1200 mL with dry tetrahydrofuran and cooled to −78° C. n-Butyllithium (310 mL of a 1.6M solution in hexane) was added, while stirring under nitrogen, at a rate to keep the temperature below −70° C. Stirring was continued at −78° C. for 45 minutes. A solution of 3-bromobenzaldehyde (100.0 g, 0.54 mol) in 900 mL of dry tetrahydrofuran was added at a rate to keep the reaction temperature below −70° C.

After stirring for 30 minutes at −78° C., the reaction was quenched with 500 mL of saturated aqueous ammonium chloride and allowed to warm to room temperature. The mixture was diluted with water and diethyl ether and the ethereal layer was washed with brine, dried over sodium sulfate and evaporated to give 216.2 g of a yellow oil. Chromatography on silica gel with hexane:ethyl acetate (4–25%) gave 98.86 g (51%) of α-3-bromophenyl)-(3-(tert-butyldimethylsilyloxy)benzyl alcohol as a yellow oil.

NMR (CDCl₃, 200 MHz) δ: 0.2 (s, 6H); 0.95 (s, 9H); 2.3 (br s, 1H); 5.7 (s, 1H); 6.75 (d, J=8 Hz, 1H); 6.8 (s, 1H); 6.9 (d, J=8 Hz, 1H); 7.2 (m, 2H); 7.3 (d, J=8 Hz, 1H); 7.4 (d, J=8 Hz, 1H); 7.5 (s, 1H).

Thionyl chloride (27.5 mL, 0.38 mol) was added dropwise to a solution of the benzhydryl alcohol from above (98.9 g, 0.25 mol) in 500 mL of dichloromethane and the mixture was stirred overnight at room temperature. The solvent was removed under vacuum, the residue was redissolved in toluene, and the solvent was again removed under vacuum to eliminate excess thionyl chloride to give 154 g of crude α-(3-bromophenyl)-3-(tert-butyldimethylsilyloxy) benzyl chloride as a brown oil.

NMR (CDCl₃, 200 MHz) δ: 0.2 (s, 6H); 0.95 (s, 9H); 6.0 (s, 1H); 6.8–7.0 (m, 3H); 7.2–7.6 (m, 5H).

A mixture of the benzhydryl chloride from above (103.5 g, 0.25 mol) and trans-1-allyl-2,5-dimethylpiperazine (96.9 g, 0.63 mol) in 50 mL of toluene was heated at reflux overnight. Acetonitrile (350 mL) and tetraethylammonium fluoride hydrate (75 g, 0.38 mol) were added to the cooled reaction mixture. After stirring at room temperature for 30 minutes, the solvent was removed under vacuum to give 344 g of a crude mixture of diastereomers as a dark brown oil. Chromatography on silica gel with dichloromethane:ethanol (99:1) gave 31.15 g of a brown solid containing 95% of the less mobile diastereomer (RF=0.42 on silica gel with dichloromethane:ethanol:ammonium hydroxide/95:5:1). Crystallization from isopropanol gave 28.6 g (55% of theoretical for one diastereomer) of (±)-3-((αR*)-α-((2R*,5S*)-4-allyl-2,5-dimethyl-1-piperazinyl)-3-bromobenzyl)phenol as a white solid, mp 186–189° C.

NMR (DMSO-d₆, 200 MHz) δ: 0.95 (d, J=6 Hz, 3H); 1.03 (d, J=6 Hz, 3H); 1.8 (dd, J1=6 Hz, J2=10 Hz, 1H); 2.1 (dd, J1=6 Hz, J2=10 Hz, 1H); 2.4–2.6 (m, 3H); 2.7 (d, J=11 Hz, 1H); 2.8 (dd, J1=7 Hz, J2=14 Hz, 1H); 3.2 (dd, J1=6 Hz, J2=13 Hz, 1H); 4.9 (s, 1H); 5.1 (d, J=10 Hz, 1H); 5.2 (d, J=18 Hz, 1H); 5.7–5.9 (m, 1H); 6.6–6.8 (m, 3H); 7.0–7.4 (m, 4H); 7.55 (s, 1H); 9.35 (s, 1H).

The bromobenzene from above (3.22 g, 7.75 mmol) was dissolved in 25 mL of dimethylformamide with cuprous cyanide (1.39 g, 15.5 mmol), and the reaction was heated at reflux for 3 days. The reaction was cooled to room temperature and poured into 300 mL aqueous 30% sodium cyanide. The mixture was extracted with 250 mL of ethyl acetate. The solvent was removed and the residue was purified by chromatography on silica gel with ethanol (0–20%) in dichloromethane to give 1.3 g (46%) of (±)-3-((αR*)-α-((2S*,5R*)-4-allyl-2,5-dimethyl-1-piperazinyl)-3-hydroxybenzyl)benzonitrile, mp 169–171° C. Calculations for C₂₃H₂₇N₃O: C, 76.42; H, 7.53; N, 11.62. Found: C, 76.35; H, 7.54; N, 11.62.

Hydrogen peroxide (0.5 mL of a 30% by weight solution) was added to a mixture of the benzonitrile (0.50 g, 1.4 mmol), 0.7 mL of 10N aqueous sodium hydroxide and 3 mL of ethanol. The reaction was exothermic with gas evolution and formation of a white precipitate. After a few minutes, the mixture was carefully heated under a reflux condenser in an oil bath at 60° C. for three hours. After cooling to room temperature, 6N aqueous hydrochloric acid was added to adjust the pH to 8. The mixture was evaporated to dryness under vacuum, and the residue was extracted between ethyl acetate and pH 8 buffer solution. The organic layer was washed with pH 8 buffer and brine, dried over sodium sulfate, and the solvent was evaporated to give 0.42 g (79%) of (±)-3-((αR*)-α-((2S*,5R*)-4-allyl-2,5-dimethyl-1-piperazinyl)-3-hydroxybenzyl)benzamide as a bright yellow solid.

NMR (200 MHz, DMSO-d₆) δ: 0.95 (d, J=6 Hz, 3H); 1.05 (d, J=6 Hz, 3H); 1.9 (m, 1H); 2.1 (m, 1H); 2.5–2.8 (m, 3H); 2.9 (m, 1H); 3.1 (m, 1H); 3.3 (br m, 1H); 4.9 (s, 1H); 5.1 (d, J=11 Hz, 1H); 5.2 (d, J=18 Hz, 1H); 5.8 (m, 1H); 6.6–6.8 (m, 3H); 7.1 (t, J=8 Hz, 1H); 7.2–7.45 (m, 2H); 7.55 (d, J=8 Hz, 1H); 7.65 (d, J=8 Hz, 1H); 7.9 (m, 2H); 9.3 (br m, 1H).

The product was dissolved in absolute ethanol and converted to the monohydrochloride salt by titration to pH 3 with ethanolic hydrogen chloride. The salt was precipitated with diethyl ether, and dried under vacuum to give 93 mg of a white powder. Calculations for C₂₃H₂₉N₃O₂ HCl 0.6 H₂O: C, 64.73; H, 7.37; N, 9.85; Cl, 8.31. Found: C, 64.81; H, 7.26; N, 9.46; Cl, 8.09.

Mass spec (CI-CH₄): m/z 380 (M+1, 76%); 379 (M+, 9%); 226 (39%); 153 (100%).

EXAMPLE 7

N,N-Diethyl-4-((αR)-3-hydroxy-α-((2R,5R)-2,5-dimethyl-1-piperazinyl)benzyl)benzamide Thionyl chloride (2.9 mL, 40.2 mmol) was added to a solution of 4-(3-(tert-butyldimethylsilyloxy)-α-hydroxybenzyl)-N,N-diethylbenzamide (11.0 g, 26.8 mmol, Example 1, infra) in 150 mL of dichloromethane. After stirring for one hour at room temperature, the solvent was removed under vacuum. The residue was dissolved in toluene and the solution evaporated under vacuum again to remove excess thionyl chloride, repeating once more. The crude product was dissolved in toluene (50 mL), and (2R, 5R)-2,5-dimethylpiperazine, prepared from D-Ala-D-Ala-diketopiperazine (Bachem Chemicals, Philadelphia, Pa.) as described in *J. Org. Chem.* 50: 4909–13, (1985), was added. The mixture was heated at reflux overnight under nitrogen. The solvent was removed under vacuum, and the residue was in redissolved in ethyl acetate and washed with 1.0 M sodium hydroxide and water. The organic layer was dried over sodium sulfate and the solvent removed to give a dark oil. The crude product was dissolved in 100 mL of acetonitrile, tetraethyl ammonium fluoride hydrate (8.07 g, 39.6 mmol) was added, and the mixture was stirred at room temperature for 30 minutes. The solvent was removed under vacuum. The residue was dissolved in 100 mL of 1N aqueous hydrochloric acid and 200 mL of diethyl ether. The aqueous layer was adjusted to pH 8 with 5M sodium hydroxide and extracted with dichloromethane (two 300 mL portions). The dichloromethane phase was dried over sodium sulfate and evaporated to dryness to give 8.03 g of a brown solid. Recrystallization from ethanol-hexane gave 1.37 g of N,N-diethyl-4-(((αR)-3-hydroxy-α-((2R,5R-2,5-dimethyl-1-piperazinyl)benzyl)benzamide (26% of theoretical yield for one diastereomer).

NMR (200 MHz, CDCl₃) δ: 0.95 (d, J=6 Hz, 3H); 1.05 (d, J=6 Hz, 3H); 1.0–1.3 (br m, 6H); 2.1 (t, J=11 Hz, 1H); 2.65 (dd, J1=3 Hz, J2=11 Hz, 1H); 2.75 (d, J=13 Hz, 1H); 3.0–3.4 (br m, 5H); 3.5 (br m, 2H); 4.5 (s, 1H); 6.65 (d, J=8 Hz, 1H); 6.8 (d, J=8 Hz, 1H); 6.9 (s, 1H); 7.1 (t, J=8 Hz, 1H); 7.3 (d, J=8 Hz, 2H); 7.5 (d, J=8 Hz, 2H).

Mass spec (CI-CH₄) m/z 395 (M, 26%); 282 (100%); 113 (21%). Calculations for C₂₄H₃₃N₃O₂ 0.5 H₂O: C, 71.26; H, 8.47; N, 10.39. Found: C, 71.32; H, 8.46; N, 10.18.

EXAMPLE 8

4-((αR)-α-((2S,5S)-4-Allyl-2,5-dimethyl-1-piperazinyl)-3-hydroxybenzyl)-N-ethyl-N-methylbenzamide Thionyl chloride (26 mL, 0.36 mol) was added dropwise to a solution of 4-carboxybenzaldehyde (50.0 g, 0.33 mol) in 2000 mL of dichloromethane:N,N-dimethylformamide (4:1 mixture). The mixture was stirred overnight at room temperature. Ethylmethylamine (75.0 g, 1.3 mol) was added dropwise, and stirring was continued at room temperature for 90 minutes. The solvent was removed under vacuum, the residue was dissolved in 500 mL of 0.1M sodium hydroxide, and extracted with ethyl acetate. The organic phase was washed with water, dried over sodium sulfate and evaporated under vacuum to give 23.8 g (38%) of N-ethyl-4-formyl-N-methylbenzamide as a yellow oil.

NMR (300 MHz, CDCl$_3$) δ: 1.1 (m, 3H); 1.2 (m, 3H); 3.2 (m, 2H); 3.5 (m, 2H); 7.5 (d, J=8 Hz, 2H); 7.9 (d, J=8 Hz, 2H); 10.0 (s, 1H).

N-Ethyl-4-formyl-N-methylbenzamide (23.8 g, 0.12 mol) was reacted with 3-(bromophenoxy)-tert-butyldimethylsilane and n-butyllithium as described in Example 5 to give 19.6 g (40%) 4-(3-(tert-butyldimethylsilyloxy)-α-hydroxybenzyl)-N-ethyl-N-methylbenzamide as a colorless oil.

NMR (200 MHz, CDCl$_3$) δ: 0.1 (s, 6H); 0.95 (s, 9H); 1.1 (m, 3H); 2.9 and 3.0 (s, 3H); 3.05 (d, J=3 Hz, 1H); 3.3 (m, 1H); 6.95 (d, J=8 Hz, 1H); 7.1 (t, J=8 Hz, 1H); 7.25 (AB quartet, J=8 Hz, 4H).

The benzhydryl alcohol (19.5 g, 0.049 mol) was treated with thionyl chloride and (2S,5S)-2,5-dimethylpiperazine as described in Example 7 to give 8.13 g (34%) of a 1:1 mixture of 4-((αR)-α-((2S,5S)-2,5-dimethyl-1-piperazinyl)-3-hydroxybenzyl)-N-ethyl-N-methylbenzamide and 4-((αS)-α-((2S,5S)-2,5-dimethyl-1-piperazinyl)-3-hydroxybenzyl)-N-ethyl-N-methylbenzamide as an off-white solid. After chromatography on silica gel (Waters Prep 500) with dichloromethane:ethanol:triethylamine (100:0.5:0.1), 0.95 g of 4-((αR)-α-((2S,5S)-2,5-dimethyl-1-piperazinyl)-3-hydroxybenzyl)-N-ethyl-N-methylbenzamide, the less mobile diastereomer, was obtained.

The product (0.77 g, 1.55 mmol) was treated with allyl bromide (0.14 mL, 1.6 mmol) as described in Example 5 to give 0.71 g of a light beige solid which was dissolved in 25 mL of acetonitrile and treated with tetraethylammonium fluoride hydrate (0.40 g) at room temperature for 30 minutes, The solvent was evaporated under vacuum and the residue was dissolved in diethyl ether and 1N aqueous hydrochloric acid. The aqueous layer was adjusted to pH 8 with 10N sodium hydroxide and extracted with dichloromethane, dried over sodium sulfate and evaporated under vacuum to give 0.51 g of 4-((αR)-α-((2S,5S)-4-allyl-2,5-dimethyl-1-piperazinyl)-3-hydroxybenzyl)-N-ethyl-N-methylbenzamide as a white solid.

NMR (200 MHz, CDCl$_3$) δ: 0.95 (d, J=6 Hz, 6H); 1.2 (br m, 3H); 2.1–2.5 (m, 4H); 2.6 (m, 1H); 2.7–2.95 (m, 2H); 3.25 (br m, 1H); 3.4 (m, 1H); 3.55 (br m, 1H); 4.45 (s, 1H); 5.1–5.2 (m, 2H); 5.8 (m, 1H); 6.6 (d, J=8 Hz, 1H); 6.9 (d, J=g Hz, 1H); 6.95 (s, 1H); 7.05 (t, J=8 H, 1H); 7.25 (d, J=8 Hz, 2H); 7.35 (d, J=8 Hz, 2H).

Conversion to the monohydrochloride salt as described in Example 6 gave 0.42 g of a white solid. Calculations for $C_{26}H_{35}N_3O_2$ HCl 0.75 $H_2O$: C, 66.22; H, 8.02; Cl, 7.52; N, 8.91. Found: C, 65.96; H, 8.02; Cl, 7.54; N, 8.92. $[α]_D^{20}$=+9.8° (abs ethanol, c=1.5). Mass spec (CI-CH$_4$) m/z: 422 (M+1, 53%); 268 (25%); 153 (100%).

EXAMPLE 9

3-((αR)-α-((2S,5S)-4-Allyl-2,5-dimethyl-1-piperazinyl)benzyl)phenol and 3-((αS)-α-((2S,5S)-4-Allyl-2,5-dimethyl-1-piperazinyl)benzyl)phenol A solution of (2S,5S)-1-allyl-4-(4-bromo-α-(3-(tert-butyldimethyl-silyloxy)phenyl)benzyl)-2,5-dimethylpiperazine (0.37 g, 0.7 mmol, Example 5, infra) in 50 mL dry tetrahydrofuran was cooled to −78° C. n-Butyllithium (0.44 mL of a 1.6M solution in hexanes) was added dropwise. After stirring at −78° C. for 10 minutes, saturated aqueous ammonium chloride (10 mL) was added. The mixture was warmed to room temperature and diluted with diethyl ether and water. The ethereal layer was dried over sodium sulfate and evaporated to give a light yellow oil, which was purified by preparative thin layer chromatography to give 0.23 g of a yellow glass. The product was dissolved in acetonitrile and treated with tetraethylammonium fluoride hydrate for 30 minutes. The solvent was evaporated under vacuum, and the residue was dissolved in 1N hydrochloric acid and extracted with diethyl ether. The aqueous layer was adjusted to pH 8 with aqueous sodium hydroxide, extracted with dichloromethane, the organic layer dried over sodium sulfate and the solvent removed to give 0.16 g of a 1:1 isomeric mixture of 3-((αR)-α-((2S,5S)-4-allyl-2,5-dimethyl-1-piperazinyl)benzyl)-phenol and 3-((αS)-α-((2S,5S)-4-allyl-2,5-dimethyl-1-piperazinyl)-benzyl)phenol as a yellow oil.

NMR (200 MHz, CDCl$_3$) δ: 0.9–1.2 (m, 6H); 2.2–2.8 (m, 5H); 2.8–3.2 (m, 2H); 3.4 (m, 1H); 4.5 (s, 0.5H); 4.6 (s, 0.5H); 5.1–5.25 (m, 2H); 5.8 (m, 1H); 6.6 (d, J=8 Hz, 1H); 6.7–7.5 (m, 8H). A portion of the product (40 mg) was dissolved in absolute ethanol and titrated to pH 4 with ethanolic hydrogen chloride. Diethyl ether was added to precipitate the monohydrochloride salt as a white solid. After drying under vacuum at 65° C. overnight, 25 mg of salt was obtained. Calculations for $C_{22}H_{28}N_2O$ HCl 0.75 $H_2O$: C, 68.12; H, 7.58; N, 7.16. Found: C, 68.38; H, 7.95; N, 7.25.

EXAMPLE 10

(±)-N,N-Diethyl-4-((αR*)-3-hydroxy-α-((2R*,S*)-2,4,5-trimethyl-1-piperazinyl)benzyl)benzamide 4-(3-(tert-Butyldimethylsilyloxy)-α-hydroxybenzyl)-N,N-diethylbenzamide (Example 1, infra) was treated with thionyl chloride and trans-2,5-dimethylpiperazine as described in Example 5. The crude mixture of diastereomers was purified by chromatography on silica gel (Waters Prep 500) with dichloromethane:ethanol:triethylamine (100:0.25:0.1). The less mobile isomer (1.28 g, 2.5 mmol) was dissolved in acetonitrile and treated with tetraethylammonium fluoride hydrate (0.6 g, 4.0 mmol) as in Example 7 to give 0.46 g of (±)-N,N-diethyl-4-((αR*)-3-hydroxy-α-((2R*,5S*)-2,5-dimethyl-1-piperazinyl)benzyl)benzamide as a white solid, mp 175–177° C.

NMR (200 MHz, DMSO-d$_6$) δ: 0.85 (d, J=6 Hz, 3H); 1.1–1.2 (m, 9H); 1.45 (m, 1H); 2.2 (m, 2H); 2.5 (m, 1H); 2.6 (m, 1H); 2.8 (m, 2H); 3.2–3.6 (m, 4H); 5.25 (s, 1H); 6.6 (d, J=8 Hz, 1H); 6.75 (d, J=8 Hz, 1H); 6.8 (s, 1H); 7.1 (t, J=8 Hz, 1H); 7.25 (d, J=8 Hz, 2H); 7.4 (d, J=8 Hz, 2H); 9.25 (s, 1H).

A mixture of the product (0.31 g, 0.78 mmol), 96% formic acid (0.12 mL, 3.1 l mmol) and 37% aqueous formaldehyde (0.06 mL, 2.3 mmol) was heated in an oil bath at 80° C. overnight. The cooled reaction mixture was dissolved in 3 mL of 6N hydrochloric acid and extracted with diethyl ether. The aqueous layer was adjusted to pH 8 with 10N sodium hydroxide, and extracted with dichloromethane. The organic layer was dried over sodium sulfate and evaporated to give a brown oil. The crude product was purified by preparative thin layer chromatography with dichloromethane:ethanol:ammonium hydroxide (95:5:1) to give 0.160 g of a yellow oil.

Crystallization from ethyl acetate gave 0.105 g of (±)-N,N-diethyl-4-((αR*)-3-hydroxy-α-((2R*,5S*)-2,4,5-trimethyl-1-piperazinyl)benzyl)benzamide as a white solid, mp 220–221° C.

NMR (200 MHz, CDCl$_3$) δ: 0.9 (d, J=6 Hz, 3H); 1.15 (d, J=6 Hz, 3H); 1.2 (br m, 6H); 1.85 (m, 1H); 2.0–2.3 (m, 2H); 2.2 (s, 3H); 2.5–2.8 (m, 3H); 3.3 (br m, 2H); 3.6 (br m, 2H); 5.25 (s, 1H); 6.6 (d, J=8 Hz, 1H); 6.8 (d, J=8 Hz, 1H); 6.85 (s, 1H); 7.05 (t, J=8 Hz, 1H); 7.15 (d, J=8 Hz, 2H); 7.35 (d, J=8 Hz, 2H). Mass spec (CI-CH$_4$) m/z 410 (M+1). Calculations for C$_{25}$H$_{35}$N$_2$O$_2$: C, 73.31; H, 8.61; N, 10.26. Found: C, 73.11; H, 8.65; N, 10.25.

EXAMPLE 11

(+)-4-((αS)-α-((2S,5S)-4-Allyl-2,5-dimethyl-1-piperazinyl)-3-hydroxybenzyl)-N,N-diethylbenzamide The procedure described in Example 1 was followed using (2S,5S)-2,5-dimethylpiperazine to give 4-((αS)-α-((2S,5S)-4-allyl-2,5-dimethyl-1-piperazinyl)-3-(tert-butyldimethylsilyloxy)benzyl)-N,N-diethylbenzamide (1.51 g). Chromatography on silica gel with dichloromethane:ethanol (1–2%) gave 0.27 g (27% of theoretical for one diastereomer) of the less mobile isomer. Treatment with tetraethylammonium fluoride in acetonitrile as in Example 1 gave 0.18 g (85%) of (+)-4-((αS)-α-((2S,5S)-4-allyl-2,5-dimethyl-1-piperazinyl)-3-hydroxybenzyl)-N,N-diethylbenzamide as a white solid.

NMR (200 MHz, DMSO-d$_6$) δ: 0.85 (d, J=6 Hz, 3H); 0.95 (d, J=6 Hz, 3H); 1.1 (br m, 6H); 2.1–2.6 (m, 5H); 2.6–2.95 (m, 2H); 3.0–3.5 (br m, 5H); 4.5 (s, 1H); 5.1 (d, J=8 Hz, 1H); 5.2 (d, J=14 Hz, 1H); 5.85 (m, 1H); 6.8 (d, J=8 Hz, 1H); 6.9 (m, 2H); 7.1 (t, J=8 Hz, 1H); 7.25 (d, J=8 Hz, 2H); 7.5 (d, J=8 Hz, 2H); 9.25 (s, 1H). Mass spec (CI) m/z: 436 (M+1, 74%); 282 (100%); 1.53 (7%). [α]$_D^{20}$=+21.6° (abs ethanol, c=1.1).

The monohydrochloride salt was prepared as in Example 1 to give 0.148 g of a white powder. Calculations for C$_{27}$H$_{37}$N$_3$O$_2$ HCl H$_2$O: C, 66.17; H, 8.24; N, 8.57; Cl, 7.23. Found: C, 66.36; H, 8.16; N, 8.66; Cl, 7.33.

The more mobile isomer from the chromatography was also isolated (0.22 g, 22% of theoretical for one diastereomer) and treated with tetraethylammonium fluoride to give 0.090 g (53%) of (+)-4-((αR)-α-((2S,5S)-4-allyl-2,5-dimethyl-1-piperazinyl)-3-hydroxybenzyl)-N,N-diethylbenzamide as a white solid.

NMR (200 MHz, DMSO-d$_6$) δ: 0.85 (d, J=6 Hz, 3H); 0.95 (d, J=6 Hz, 3H); 1.1 (br m, 6H); 2.1–2.5 (m, 5H); 2.8 (m, 1H); 3.0 (m, 1H); 3.05–3.5 (br m, 5H); 4.5 (s, 1H); 5.1 (d, J=10 Hz, 1H); 5.2 (d, J=15 Hz, 1H); 5.8 (m, 1H); 6.6 (d, J=8 Hz, 1H); Hz, 1H); 7.3 (d, J=8 Hz, 2H); 7.5 (d, J=8 Hz, 2H); 9.25 (s, 1H). Mass spec (CI) m/z: 436 (M+1, 3.7%); 282 (100%); 153 (3%). [α]$_D^{20}$=+28.7° (abs ethanol, c=2.3).

The monohydrochloride salt was prepared as in Example 1 to give 0.061 g of a white powder . Calculations for C$_{27}$H$_{37}$N$_3$O$_2$ HCl 0.75 H$_2$O: C, 66.78; H, 8.20; N, 8.65; Cl, 7.30. Found: C, 66.55; H, 8.07; N, 8.63; Cl, 7.35.

EXAMPLE 12

In Vitro Delta Opioid Receptor Activity

Selected compounds of the present invention, identified below with reference to the appertaining synthesis Examples hereof, were evaluated for in vitro delta opioid receptor affinity in rat brain membranes (Delta Receptor IC$_{50}$) and delta opioid agonist potency in the mouse vas deferens (Mouse Vas Deferens ED$_{50}$). The assay procedures used for such determinations of delta receptor activity are set out below.

In vitro bioassays: Vasa deferentia were removed from mice and suspended between platinum electrodes with 0.5 g of tension in organ bath chambers containing a modified Krebs' buffer of the following composition (millimolar): NaCl, 118; KCl, 4.75; CaCl$_2$, 2.6; KH$_2$PO$_4$, 1.20; NaHCO$_3$, 24.5; and glucose, 11. The buffer was saturated with 95% O$_{2/5}$% CO$_2$ and kept at 37° C. Tissues were stimulated at supramaximal voltage with 10 Hz pulse trains for 400 msec.; train interval 10 seconds; and 0.5 msec pulse duration. The percentage inhibition of the electrically induced muscle contractions was determined for the compounds at varying cumulative concentrations. The ED$_{50}$ values were extrapolated from curves showing the dose concentration plotted against the response (Lord, et al., *Nature* 267, 495, (1977)).

Inhibition of receptor binding: Rat (Sprague-Dawley) brain membranes were prepared and binding assays were performed at 24° C. for 90 minutes as described by Chang, et al. (*J. Biol. Chem.* 254, 2610 (1979) and *Mol. Pharmacol.* 16, 91 (1979)) with a filtration method (GF/C filter). Delta receptor binding assays were performed with ($^3$H)-(+)-4-((α-R*)-α-((2S*,5R*)-4-Allyl-2,5-dimethyl-1-piperazinyl)-3-hydroxybenzyl)-N,N-diethylbenzamide (0.1 nM), having an activity of ~48 Ci/mmole, or with $^3$H-[D-Pen$^2$,D-Pen$^5$-(enkephalin)]($^3$H-DPDPE, 0.1 nM) having an activity of ~50 Ci/mmole. Non-specific binding was determined in the presence of 1 mM of the unlabeled ligand. The potency of compounds in inhibiting the binding of ($^3$H)-(+)-4-((α-R*)-α-((2S*,5R*)-4-Allyl-2,5-dimethyl-1-piperazinyl)-3-hydroxy-benzyl)-N,N-diethylbenzamide or $^3$H-DPDPE was determined as the concentration which reduced the binding of the labeled compounds by 50 percent (Delta Receptor IC$_{50}$).

The following compounds of the invention were also tested.

Compound 12:
3-((αR)-4-(piperidinocarbonyl)-α-((2S,5S)-2,4,5-trimethyl-1-piperazinyl)benzyl)phenol Compound 13:
3-((αR)-4-(1-pyrrolidinylcarbonyl)-α-((2S,5S)-2,4,5-trimethyl-1-piperazinyl)benzyl)phenol Compound 14:
(+)N,N-Diethyl-4-(3-hydroxy-(αS)-α-((2S,5S)-2,4,5-trimethyl-1-piperazinyl)benzyl)-benzamide Compound 15:
N,N-diethyl-4-(3-hydroxy-(αR)-α-((2R,5R)-2,4,5-trimethyl-1-piperazinyl)benzyl)benzamide (see, for example, International Publication WO 93/15062, Example 13 for the synthesis of this compound)

Compound 16:
N-ethyl-4-((αR)-3-hydroxy-α-((2S,5S)-2,4,5-trimethyl-1-piperazinyl)benzyl)-N-methylbenzamide Compound 17:
cis-4-(α-(4-((Z)-2-butenyl)-3,5-dimethyl-1-piperazinyl)-3-hydroxybenzyl)-N,N-diethylbenzamide (see, for example, International Publication WO 93/15062, Example 11 for the synthesis of this compound)

Compound 18:
(±)-3-((αR*)-α-((2R*,5S*)-4-allyl-2,5-dimethyl-1-piperazinyl)-4-(methylsulfonyl)benzyl)phenol (see, for example, International Publication WO 93/15062, Example 55 for the synthesis of this compound)

Compound 19:

(±)-4-((αR*)-α-((2R*,5S*)-4-Allyl-2,5-dimethyl-1-piperazinyl)-3-hydroxybenzyl)-N,N-dimethylbenzenesulfonamide (see, for example, International Publication WO 93/15062, Example 56 for the synthesis of this compound)

Compound 20:

(±)-3-((αR*)-α-((2S*,5R*)-4-Allyl-2,5-dimethyl-1-piperazinyl)benzyl)phenol (see, for example, International Publication WO 93/15062, Example 10 for the synthesis of this compound)

Compound 21:

(±)-4-((αR*)-α-((2S*,5R*)-4-Allyl-2,5-dimethyl-1-piperazinyl)-3-hydroxybenzyl)benzamide (see, for example, International Publication WO 93/15062, Example 4 for the synthesis of this compound)

Compound 22:

(±)-4-((αR*)-α-((2R*,5S*)-2,5-Dimethyl-1-piperazinyl)-3-hydroxybenzyl)-N,N-diethylbenzamide (see, for example, International Publication WO 93/15062, Example 15 for the synthesis of this compound)

Compound 23:

(±)-cis-4-(α-(4-Allyl-3,5-dimethyl-1-piperazinyl)-3-hydroxybenzyl)-N,N-diethylbenzamide Compound 24:

cis-4-(α-(3,5-Dimethyl-4-(methylallyl)-1-piperazinyl)-3-hydroxybenzyl)-N,N-diethylbenzamide Results are shown in Table A below, with the compounds described in Examples 1–11 being listed as Compounds 1–11, respectively.

TABLE A

In Vitro Delta Opioid Receptor Activity of Compounds of the Invention

| Compound | Delta Receptor $IC_{50}$ (nM) | Mouse Vas Deferens $ED_{50}$ (nM) |
| --- | --- | --- |
| 1 | 2[a] | 43 |
| 2 | 1[a] | — |
| 3 | — | — |
| 4 | — | >1,000 |
| 5 | 1.6 | 260 |
| 6 | 4.0 | 25 |
| 7 | 1.1 | 560 |
| 8 | 0.86 | 30 |
| 9 | 1.5 | 450 |
| 10 | 1.1 | 90 |
| 11 | — | — |
| 12 | 1.2 | 250 |
| 13 | 0.8 | 200 |
| 14 | 2 | $pA_2 = 7.1$[b] |
| 15 | 2.8 | $pA_2 = 7.0$[b] |
| 16 | 3.1 | $pA_2 = 7.2$[b] |
| 17 | 1.5 | $pA_2 = 8.2$[c] |
| 18 | 1.3 | 250 |
| 19 | 2.6 | 37 |
| 20 | 1.3 | 78 |
| 21 | 1.6 | 44 |
| 22 | 0.7 | 4400 |
| 23 | 3.3 | 42 |
| 24 | 2.8 | 20 |

[a]Compounds 1 and 2 were assayed against ($^3$H)-(+)-4-((α-R*)-α-((2S*, 5R*)-4-Allyl-2,5-dimethyl-1-piperazinyl)-3-hydroxybenzyl)-N,N-diethylbenzamide. Compounds 5–24 were assayed against $^3$H-[D-Pen$^2$, D-Pen$^5$]-(enkephalin).
[b], [c]Antagonist potency ($pA_2$ value) as determined by Schild analysis, according to Arunlakshana et al., Brit. J. Pharmacol. 14:48–58 (1979), of data for blockade of inhibitory effect of [D-Ala$^2$, D-Leu$^5$] enkephalin ([b]) or (±)-4-((α-R*)-α-((2S*, 5R*)-4-Allyl-2,5-dimethyl-1-piperazinyl)-3-hydroxybenzyl)-N,N-diethylbenzamide ([c]) on electrically stimulated muscle contraction in the mouse vas deferens.

EXAMPLE 13

Effects of the Compounds of Example 1 and Example 2 on Alfentanil Induced Analgesia and Respiratory Depression in Rats Analgesia was assayed in rats using the tail pinch test with simultaneous monitoring of capillary blood gases ($pCO_2$ and $pO_2$) using a transcutaneous electrode. Male Sprague Dawley rats (groups of six animals) were anesthetized with 2% isoflurane (J. A. Webster, Inc., Sterling, Mass.), and a cannula was implanted into the right external jugular vein. A small patch of skin was shaved on the back of the animals and a fixation ring was attached using VetBond adhesive (3M Corp., Minneapolis, Minn.). The transcutaneous electrode of a TCM3 TINA™ blood gas monitor system (Radiometer-Copenhagen, Copenhagen, Denmark) was attached to the fixation ring and the rats were allowed to recover from the anesthetic for 1 hour. The mu-opioid analgesic alfentanil (Janssen Pharmaceuticals, Inc., Titusville, N.J.) was administered by continuous infusion via i.v. cannula at a dose of 6 μg/kg/min with concurrent administration of delta-opioid test compounds. Analgesia was assayed before and during dosing using the tail pinch test. An artery clamp was placed on the tail one inch from the tip for a maximum of 20 seconds. Rats were observed for nociceptive responses of vocalization or painful body movements. The elapsed time to elicit a pain response was recorded as the tail pinch latency in seconds. Blood gases were monitored continuously throughout the test session.

After 15 minutes of infusion, the alfentanil dose of 6 μg/kg/min produced a maximum analgesic effect as indicated by a tail pinch latency of 20 seconds. Respiratory depression was measured at an average of 30% increase in $pCO_2$ level (above preinfusion baseline). Concurrent infusion of the compound of Example 1 at a dose of 60 μg/kg/min partially reversed the respiratory depression to a $pCO_2$ level of 22% above baseline. Increasing the dose of the compound of Example 1 to 120 μg/kg/min produced a further improvement in respiratory depression to 17% above baseline. Tail pinch latency remained unaffected by treatment with the compound of Example 1.

When the compound of Example 2 was infused at a dose of 60 μg/kg/min concurrently with alfentanil (6 μg/kg/min) and the compound of Example 1 (60 μg/kg/min), the effects of the compound of Example 1 were blocked and respiratory depression increased to a $pCO_2$ level of 33% above baseline. Analgesia remained unaffected, with tail pinch latency continuing to be at the maximum of 20 seconds. In separate experiments, administration of the compound of Example 1 alone or the compound of Example 2 alone produced no analgesic effect and no effect on blood $pCO_2$ levels.

EXAMPLE 14

A series of experiments were carried out to determine the effects of delta agonists on respiratory depression and analgesia induced by i.v. infusions of alfenta or fentanyl, very potent mu agonists. Two different methods were used to measure respiratory depression effects. The first method analyzed rat blood gases for $pCO_2$ levels. Rat blood samples were drawn and analyzed for $CO_2$ content following a continuous i.v. infusion of alfenta (6 mg/min) and an i.v. bolus injection of various doses of the selective delta agonist, BW373U86:

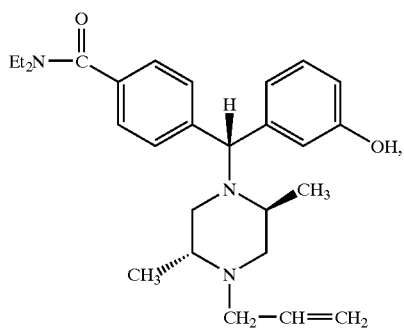

(+)-4-((αR)-α-((2S,5R)-4-allyl-2,5-dimethyl-1-piperazinyl)-3-hydroxybenzyl)-N,N-diethylbenzamide.

As an indication of respiratory depression, blood $CO_2$ levels were observed to increase as a result of alfenta administration. The key finding in the experiment, however, was that BW373U86 dose dependently reduced the level of $pCO_2$ seen following the alfenta infusion. Results are depicted in FIGS. 1A and 1B.

Figure 1B:
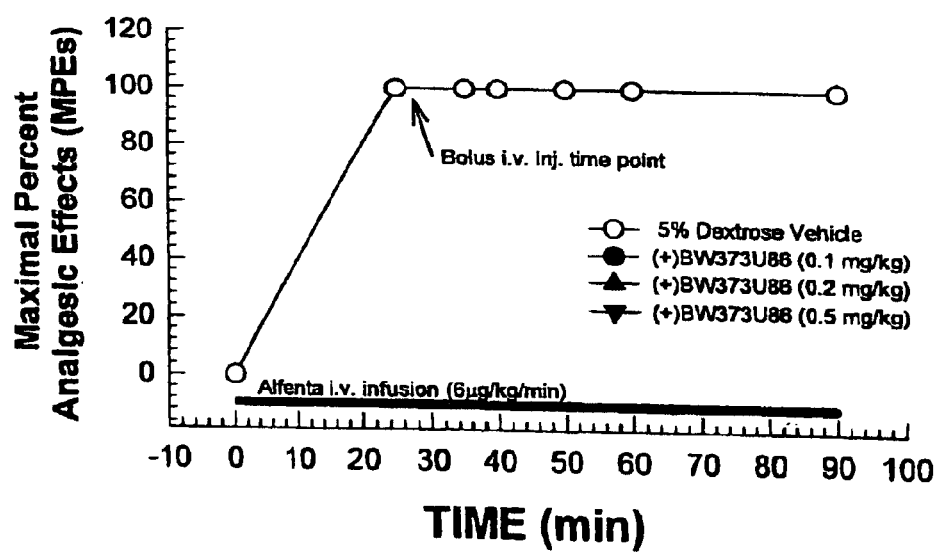
FIG. 1B shows the effect of the delta agonist BW373U86 on analgesia induced by the mu agonist, alfenta.

FIGS. 1A and 1B show the effect of the positive isomer of the delta agonist BW373U86 on analgesia and respiratory depression induced by the mu agonist, alfenta. (+)373U86 blocks the respiratory depression (as shown by FIG. 1A), but not the analgesia induced by alfenta (as shown by FIG. 1B). The negative isomer of 373U86 does not have any significant effects on alfenta-induced respiratory depression (data not shown). All doses of BW373U86 are plotted in the analgesia graph, however some points cannot be seen because the symbols are overlapping.

Analgesia was also assessed with a tail-pinch method at the same time points that blood was drawn. Most importantly, BW373U86 did not significantly affect the analgesia produced by alfenta (FIG. 1B). Overall, the data indicate that BW373U86, or other delta agonists, are useful clinically in intraoperative, postoperative and chronic pain applications to attenuate the respiratory depression and maintain the analgesic effects of mu opioid receptor analgesics.

A second method was used to quantify respiratory depression effects in subsequent studies. These studies utilized a transcutaneous $pO_2/pCO_2$ non-invasive monitoring system (Radiometer Copenhagen). The system monitors $O_2$ and $CO_2$ levels through an electrode that is adhered to the outside skin surface. These systems are typically used on infants in hospital critical care centers and were adapted for use with rats for the present studies. Rats were implanted with a catheter in the right external jugular vein under 2% isoflurane anesthesia. Subjects were allowed to recover for 1 hr and then were placed in plastic restraining cages. Testing began after baseline measures of $pCO_2$ and $pO_2$ were obtained over a 15 min period.

Both fentanyl (a strong mu-receptor analgesic agent) and 3290W93 (a compound with mixed delta and mu receptor activity), whose chemical structure is shown below:

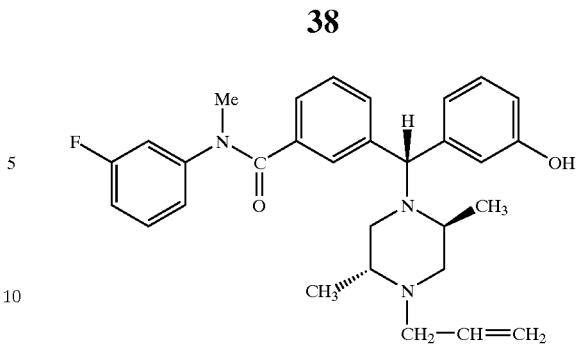

were found to produce high levels of analgesia. Results are depicted in FIGS. 2A and 2B.

Figure 2A:
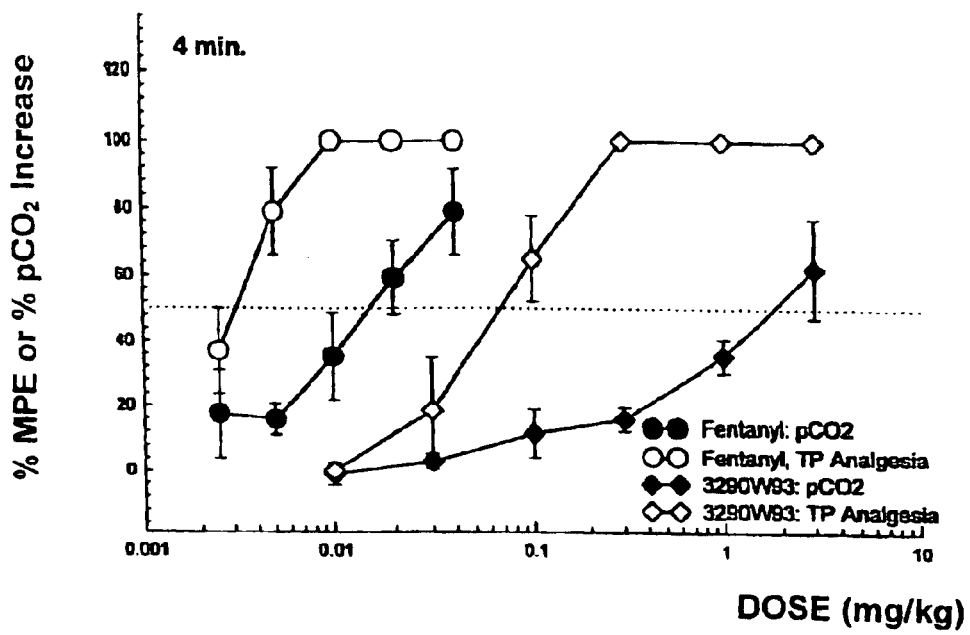
FIG. 2A shows the analgesic and respiratory depression effects of 3290W93 and fentanyl in rats, plotted at 4 minute time points at which times peak effects were observed following drug administration.
Figure 2B:
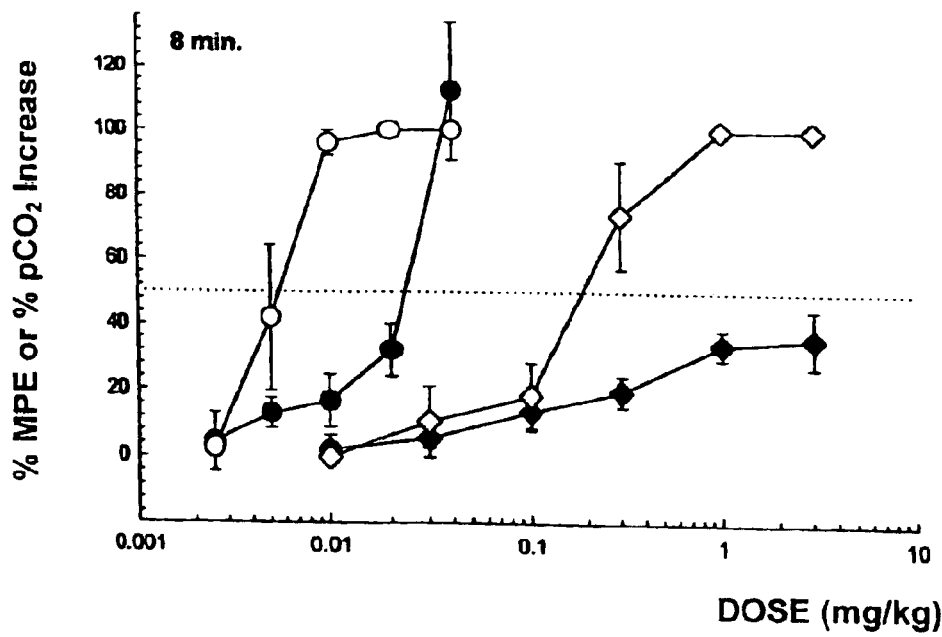
FIG. 2B shows the analgesic and respiratory depression effects of 3290W93 and fentanyl in rats, plotted at 8 minute time points.

FIGS. 2A and 2B show comparative analgesic and respiratory depression effects of 3290W93 and fentanyl in rats. Effects are plotted at 4 (FIG. 2A) and 8 (FIG. 2B) minute time points at which peak effects were observed following drug administration. A greater separation between analgesic and respiratory depressant effects occurred following 3290W93 administration than was observed following fentanyl administration.

However, whereas fentanyl produced high levels of respiratory depression, 3290W93 did not substantially increase respiratory depression except at high doses. The $ED_{50}$ values in rats for fentanyl and 3290W93 to produce analgesia were 0.0031 and 0.08 mg/kg (i.v.), respectively. The $ED_{50}$ values for fentanyl and 3290W93 to produce respiratory depression are 0.014 and 2.0 mg/kg (i.v.), respectively. The therapeutic ratio (respiratory depression ED50 divided by analgesia ED50) for fentanyl and 3290W93 are 4.5 and 25, respectively. These data indicate that the mixed delta/mu agonist 3290W93 has a five times greater separation between analgesic and respiratory depressant effects than does fentanyl.

As shown in FIGS. 1 and 2, a delta receptor agonist can selectively block effects produced by the mu opioid receptor agonists alfenta and fentanyl. Typically, mu agonists produce a substantial beneficial effect of analgesia and many adverse side effects, such as respiratory depression, nausea, addiction and dependence. The ability to use delta receptor compounds to block the unwanted side effects of mu agonists permits physicians to increase the administration of analgesics because of reduced concerns about respiratory depression. Patients experience less pain after an operation and require less postoperative care by hospital staff. The overall lifestyle of patients taking mu opioids may be significantly improved with the concurrent use of delta receptor compounds.

In addition to the delta agonist compounds described specifically above, the compounds disclosed in International Patent Publications WO96/36620 and WO97/10230 may advantageously be employed in the broad practice of the present invention, to antagonistically modulate the respiratory depression effects incident to the use of morphine, fentanyl and other analgesics, Esthetics and barbiturates, as well as any other opioid receptor therapeutic agents which mediate respiratory depression as an effect of their physiological activity.

While the invention has been illustratively described herein with respect to various illustrative aspects, features and embodiments, it will be appreciated that numerous variations, modifications and other embodiments are possible in the practice of the present invention, and the invention therefore is to be broadly construed as encompassing all such variations, modifications and other embodiments, within its spirit and scope.

We claim:
1. A pharmaceutical composition comprising:
   (1) an effective amount of a bioactive compound mediating respiratory depression, muscle rigidity, and/or nausea/vomiting as an unwanted side effect thereof; and
   (2) a non-polypeptide δ receptor activating agent effective for combating said side effect.
2. The pharmaceutical composition of claim 1, wherein the δ receptor activating agent comprises a diarylmethylpiperazine or a diarylmethylpiperdine compound.
3. The pharmaceutical composition of claim 1, wherein the δ receptor activating agent comprises a diarylmethylpiperazine compound.
4. The pharmaceutical composition of claim 1, wherein the δ receptor activating agent comprises 3290W93.
5. The pharmaceutical composition of claim 1, wherein the δ receptor activating agent comprises BW373U86.
6. The pharmaceutical composition of claim 1, wherein the δ receptor activating agent comprises an agent selected from the group consisting of:
   I. diarylmethylpiperazine compounds;
   II. diarylmethylpiperidine compounds;
   III. deltorphin I; and
   IV. deltorphin II.
7. The pharmaceutical composition of claim 1, wherein the δ receptor activating agent comprises an agent selected from the group consisting of:
   I. δ agonist compounds of the formula:

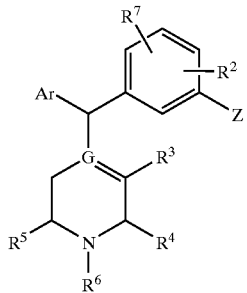

(I)

wherein:
Ar is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent $R^1$;
Y is selected from the group consisting of:
   hydrogen;
   halogen;
   $C_1$–$C_6$ alkyl, $C_2$–$C_6$ alkenyl, $C_2$–$C_6$ alkynyl;
   $C_1$–$C_6$ haloalkyl;
   $C_1$–$C_6$ alkoxy;
   $C_3$–$C_6$ cycloalkoxy;
   sulfides of the formula $SR^8$ where $R^8$ is $C_1$–$C_6$ alkyl, $C_2$–$C_6$ alkenyl, $C_2$–$C_6$ alkynyl, $C_3$–$C_6$ cycloalkyl, arylalkyl having a $C_5$–$C_{10}$ aryl moiety and an $C_1$–$C_6$ alkyl moiety, or $C_5$–$C_{10}$ aryl;
   sulfoxides of the formula $SOR^8$ where $R^8$ is the same as above;
   sulfones of the formula $SO_2R^8$ where $R^8$ is the same as above;
   nitrile;
   $C_1$–$C_6$ acyl;
   alkoxycarbonylamino (carbamoyl) of the formula $NHCO_2R^8$ where $R^8$ is the same as above;
   carboxylic acid, or an ester, amide, or salt thereof;
   aminomethyl of the formula $CH_2NR^9R^{10}$ where $R^9$ and $R^{10}$ may be the same or different, and may be hydrogen, $C_1$–$C_6$ alkyl, $C_2$–$C_6$ alkenyl, $C_2$–$C_6$ alkynyl, $C_2C_6$ hydroxyalkyl, $C_2$–$C_6$ methoxyalkyl, $C_3$–$C_6$ cycloalkyl, or $C_5$–$C_{10}$ aryl, or $R^9$ and $R^{10}$ together may form a ring of 5 or 6 atoms, the ring atoms selected from the group consisting of N and C;
   carboxamides of the formula $CONR^9R^{10}$ where $R^9$ and $R^{10}$ are the same as above, or $C_2$–$C_{30}$ peptide conjugates thereof; and
   sulfonamides of the formula $SO_2NR^9R^{10}$ where $R^9$ and $R^{10}$ are the same as above;
Z is selected from the group consisting of:
   hydroxyl, and esters thereof;
   hydroxymethyl, and esters thereof; and
   amino, and carboxamides and sulfonamides thereof;
G is carbon or nitrogen;
$R^1$ is hydrogen, halogen, or $C_1$–$C_4$ alkyl, $C_2$–$C_4$ alkenyl, $C_1$–$C_4$ alkynyl;
$R^2$ is hydrogen, halogen, or $C_1$–$C_4$ alkyl, $C_2$–$C_4$ alkenyl, $C_1$–$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
   hydrogen;
   $C_1$–$C_6$ alkyl, $C_2$–$C_6$ alkenyl, $C_2$–$C_6$ alkynyl;
   $C_3$–$C_6$ cycloalkyl;
   arylalkyl having $C_5$–$C_{10}$ aryl and $C_1$–$C_6$ alkyl moieties;
   alkoxyalkyl having $C_1$–$C_4$ alkoxy and $C_1$–$C_4$ alkyl moieties;
   $C_2$–$C_4$ cyanoalkyl;
   $C_2$–$C_4$ hydroxyalkyl;
   aminocarbonylalkyl having a $C_1$–$C_4$ alkyl moiety; and
   $R^{12}COR^{13}$, where $R^{12}$ is $C_1$–$C_4$ alkylene, and $R^{13}$ is $C_1$–$C_4$ alkyl or $C_1$–$C_4$ alkoxy; and
$R^7$ is hydrogen or fluorine,
or a pharmaceutically acceptable ester or salt thereof;
   II. delta agonist compounds of the formula:

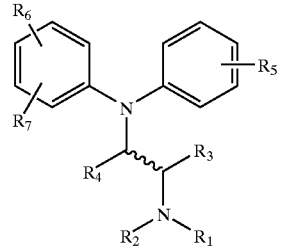

in which,
$R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen;

$R_3$ and $R_4$, which can be the same or different, are each hydrogen, linear or branched $C_{1-6}$ alkyl, or $R_4$ is oxygen forming with the carbon atom to which is attached a C=O group;

$R_5$ is hydrogen, hydroxy, $C_{1-3}$ alkoxy, thiol or alkylthio;

$R_6$ is phenyl, halogen, $NH_2$ or a para or meta —C(Z)-$R_8$ group, in which Z is oxygen or sulphur;

$R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or $R_6$ is a para or metal —N—C(Z)-$R_{12}$

group in which $R_{11}$ and $R_{12}$ which may the same or different are hydrogen, straight or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring, and Z is as defined above; and, $R_7$ is hydrogen, straight or branched $C_{1-8}$ alkyl or halogen; and III. delta agonist compounds of the formula:

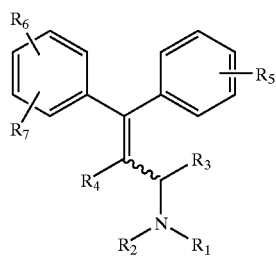

in which, $R_1$ and $R_2$, which can be the same or different, are each hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-6}$ alkenyl, $C_{3-5}$ alkynyl, aryl, aralkyl or furan-2 or 3-yl alkyl or may form together a $C_{3-7}$ alkyl ring which may be interrupted by oxygen;

$R_3$ and $R_4$, which can be the same or different, are each hydrogen, linear or branched $C_{1-6}$ alkyl;

$R_5$ is hydroxy, $C_{1-6}$ alkoxy, thiol or alkylthio;

$R_6$ is a —C(Z)-Rg group, in which Z is oxygen or sulphur, $R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{1-6}$ cycloalkylalkyl, $C_{3-6}$ alkenyl, aryl or aralkyl, or $R_6$ is a

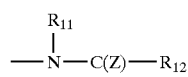

group in which $R_{11}$ and $R_{12}$ have the same meaning as $R_9$ and $R_{10}$ or together form an optionally substituted hetero-cyclic ring and Z is as defined above, and $R_7$ is hydrogen, straight or branched $C_{1-8}$ alkyl or halogen.

8. The pharmaceutical composition of claim 1, in a form suitable for injectable or spinal administration.

9. A pharmaceutical composition comprising:
   (a) an effective amount of a bioactive compound mediating respiratory depression; and
   (b) an effective amount of a non-polypeptide o receptor activating agent effective for combating said respiratory depression.

10. A pharmaceutical composition comprising an effective amount of a bioactive composition mediating respiratory depression, and an effective amount of a compound for reducing, treating or preventing respiratory depression, of the formula:

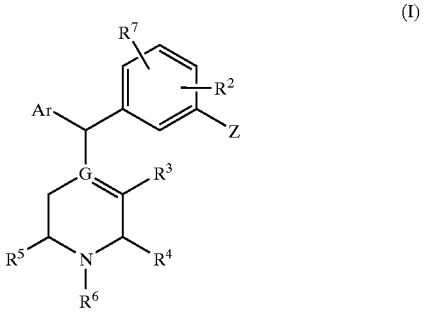

(I)

wherein:

Ar is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent $R^1$;

Y is selected from the group consisting of:

hydrogen;

halogen;

$C_1$–$C_6$ alkyl, $C_2$–$C_6$ alkenyl, $C_2$–$C_6$ alkynyl;

$C_1$–$C_6$ haloalkyl;

$C_1$–$C_6$ alkoxy;

$C_3$–$C_6$ cycloalkoxy;

sulfides of the formula $SR^8$ where $R^8$ is $C_1$–$C_6$ alkyl, $C_2$–$C_6$ alkenyl, $C_2$–$C_6$ alkynyl, $C_3$–$C_6$ cycloalkyl, arylalkyl having a $C_5$–$C_{10}$ aryl moiety and an $C_1$–$C_6$ alkyl moiety, or $C_5$–$C_{10}$ aryl;

sulfoxides of the formula $SOR^8$ where $R^8$ is the same as above;

sulfones of the formula $SO_2R^8$ where $R^8$ is the same as above;

nitrile;

$C_1$–$C_6$ acyl;

alkoxycarbonylamino (carbamoyl) of the formula $NHCO_2R^8$ where $R^8$ is the same as above;

carboxylic acid, or an ester, amide, or salt thereof;

aminomethyl of the formula $CH_2NR^9R^{10}$ where $R^9$ and $R^{10}$ may be the same or different, and may be hydrogen, $C_1$–$C_6$ alkyl, $C_2$–$C_6$ alkenyl, $C_2$–$C_6$ alkynyl, $C_2$–$C_6$ hydroxyalkyl, $C_2$–$C_6$ methoxyalkyl, $C_3$–$C_6$ cycloalkyl, or $C_5$–$C_{10}$ aryl, or $R^9$ and $R^{10}$ together may form a ring of 5 or 6 atoms, the ring atoms selected from the group consisting of N and C;

carboxamides of the formula $CONR^9R^{10}$ where $R^9$ and $R^{10}$ are the same as above, or $C_2$–$C_{30}$ peptide conjugates thereof; and sulfonamides of the formula $SO_2NR^9R^{10}$ where $R^9$ and $R^{10}$ are the same as above;

Z is selected from the group consisting of:
  hydroxyl, and esters thereof;
  hydroxymethyl, and esters thereof; and
  amino, and carboxamides and sulfonamides thereof;
G is carbon or nitrogen;
$R^1$ is hydrogen, halogen, or $C_1$–$C_4$ alkyl, $C_2$–$C_4$ alkenyl, $C_1$–$C_4$ alkynyl;
$R^2$ is hydrogen, halogen, or $C_1$–$C_4$ alkyl, $C_2$–$C_4$ alkenyl, $C_1$–$C_4$ alkynyl;
$R^3$, $R^4$ and $R^5$ may be the same or different, and are independently selected from hydrogen and methyl, and wherein at least one of $R^3$, $R^4$ or $R^5$ is not hydrogen, subject to the proviso that the total number of methyl groups does not exceed two, or any two of $R^3$, $R^4$ and $R^5$ together may form a bridge of 1 to 3 carbon atoms;
$R^6$ is selected from the group consisting of:
  hydrogen;
  $C_1$–$C_6$ alkyl, $C_2$–$C_6$ alkenyl, $C_2$–$C_6$ alkynyl;
  $C_3$–$C_6$ cycloalkyl;
  arylalkyl having $C_5$–$C_{10}$ aryl and $C_1$–$C_6$ alkyl moieties;
  alkoxyalkyl having $C_1$–$C_4$ alkoxy and $C_1$–$C_4$ alkyl moieties;
  $C_2$–$C_4$ cyanoalkyl;
  $C_2$–$C_4$ hydroxyalkyl;
  aminocarbonylalkyl having a $C_1$–$C_4$ alkyl moiety; and
  $R^{12}COR^{13}$, where $R^{12}$ is $C_1$–$C_4$ alkylene, and $R^{13}$ is $C_1$–$C_4$ alkyl or $C_1$–$C_4$ alkoxy; and
$R^7$ is hydrogen or fluorine,
or a pharmaceutically acceptable ester or salt thereof.

11. The pharmaceutical composition according to claim 10, wherein Ar is a 6-member carbocyclic aromatic (benzene) ring and $R^1$ is hydrogen.

12. The pharmaceutical composition according to claim 10, wherein Y is a carboxamide of the formula $CONR^9R^{10}$.

13. The pharmaceutical composition according to claim 10, wherein $R^9$ and $R^{10}$ together form a ring of five or six atoms, thereby forming a pyrrolidinyl or piperdine ring.

14. The pharmaceutical composition according to claim 10, wherein $R^9$ and $R^{10}$ are the same or different and are each independently selected from hydrogen, $C_1$ alkyl and $C_2$ alkyl.

15. The pharmaceutical composition according to claim 10, wherein Y is hydrogen.

16. The pharmaceutical composition according to claim 10, wherein Y is a sulfone of the formula $SO_2R^8$ and $R^8$ is $C_1$–$C_6$ alkyl.

17. The pharmaceutical composition according to claim 10, wherein G is N, $R^7$ and $R^2$ are each hydrogen, and Z is hydroxyl.

18. The pharmaceutical composition according to claim 10, wherein $R^6$ is selected from the group consisting of hydrogen, $C_1$–$C_6$ alkyl, $C_2C_6$ alkenyl and $C_2$–$C_6$ alkynyl.

19. The pharmaceutical composition according to claim 10, wherein $R^3$, $R^4$ and $R^5$ are hydrogen or methyl, where the total number of methyl groups is one or two.

20. The pharmaceutical composition according to claim 10, wherein $R^3$ and $R^5$ are both methyl, and $R^4$ is hydrogen.

21. The pharmaceutical composition according to claim 1, wherein the δ receptor activating agent comprises a compound selected from the group consisting of:
  (−)-4-((αR)-α-((2R,5R)-4-allyl-2,5-dimethyl-1-piperazinyl)-3-hydroxybenzyl)-N,N-diethyl-benzamide;
  (−)-4-((αR)-α-((2R,5R)-2,5-dimethyl-4-propyl-1-piperazinyl)-3-hydroxybenzyl)-N,N-diethyl-benzamide;
  4-((αR)-α-(2S,5S)-4-allyl-2,5-dimethyl-1-piperazinyl)-3-hydroxybenzyl)benzamide;
  (±)-3-((αR*)-α-((2S*,5R*)-4-allyl-2,5-dimethyl-1-piperazinyl)-3-hydroxybenzyl)benzamide;
  N,N-diethyl-4-((αR)-3-hydroxy-α-((2R,5R)-2,5-dimethyl-1-piperazinyl)benzyl)benzamide;
  4-((αR)-α-((2S,5S)-4-allyl-2,5-dimethyl-1-piperazinyl)-3-hydroxybenzyl)-N-ethyl-N-methyl-benzamide;
  3-((αR)-α-((2S,5S)-4-allyl-2,5-dimethyl-1-piperazinyl)benzyl)phenol;
  (±)-N,N-diethyl-4-((αR*)-3-hydroxy-α-((2R*,5S*)-2,4,5-trimethyl-1-piperazinyl)benzyl)-benzamide;
  (+)-4-((αS)-α-((2S,5S)-4-allyl-2,5-dimethyl-1-piperazinyl)-3-hydroxybenzyl)-N,N-diethyl-benzamide;
  3-((αR)-4-(piperidinocarbonyl)-α-((2S,5S)-2,4,5-trimethyl-1-piperazinyl)benzyl)phenol;
  3-((αR)-4-(1-pyrrolidinylcarbonyl)-α-((2S,5S)-2,4,5-trimethyl-1-piperazinyl)benzyl)phenol;
  (±)-3-((αR*)-α-((2R*,5S*)-4-allyl-2,5-dimethyl-1-piperazinyl)-4-(methylsulfonyl)benzyl)-phenol;
  (+)-4-((αR*)-α-((2R*,5S*)-4-allyl-2,5-dimethyl-1-piperazinyl)-3-hydroxybenzyl)-N,N-dimethylbenzenesulfonamide;
  (+)-4-((αR)-α-((2R,5S)-4-allyl-2,5-dimethyl-1-piperazinyl)-3-hydroxybenzyl)-N,N-dimethylbenzenesulfon-amide; or
  (−)-4-((αR)-α-((2R,5S)-4-allyl-2,5-dimethyl-1-piperazinyl)-3-hydroxybenzyl)-N,N-dimethylbenzenesulfonamide;
  (±)-3-((αR*)-α-((2S*,5R*)-4-allyl-2,5-dimethyl-1-piperazinyl)benzyl)phenol;
  (±)-4-((αR*)-α-((2S*,5R*)-4-allyl-2,5-dimethyl-1-piperazinyl)-3-hydroxybenzyl)benzamide;
  (±)-4-((αR*)-α-((2R*,5S*)-2,5-dimethyl-1-piperazinyl)-3-hydroxybenzyl)-N,N-diethyl-benzamide;
  (+)-cis-4-(α-(4-allyl-3,5-dimethyl-1-piperazinyl)-3-hydroxybenzyl)-N,N-diethylbenzamide;
  cis-4-(α-(3,5-dimethyl-4-(methylallyl)-1-piperazinyl)-3-hydroxybenzyl)-N,N-diethylbenzamide;
and pharmaceutically acceptable salts thereof.

22. The pharmaceutical composition of claim 1, wherein the δ receptor activating agent comprises
  (−)-4-((αR)-((2R,5R)-4-ally-2,5-dimethyl-1-piperazinyl)-3-hydroxybenzyl)-N,N-diethylbenzamide or a pharmaceutically acceptable salt thereof.

23. The pharmaceutical composition of claim 1, wherein the bioactive compound comprises an opiate compound.

24. The pharmaceutical composition of claim 1, wherein the bioactive compound comprises an opiate analgesic compound.

25. The pharmaceutical composition of claim 1, wherein the bioactive compound comprises a μ opiate compound.

26. The pharmaceutical composition of claim 1, wherein the bioactive compound comprises at least one active ingredient selected from the group consisting of alcohol, aldesleukin, alfentanil, bremazocine, buprenorphine, butorphanol, chloropromazine, clozapine, codeine, dantrolene, diazepam, dihydrocodeine, etorphine, fentanyl, flurazepam, heroin, hydrocodone, hydromorphone, ketamine, larazepam, levallorphen, levorphanol, meperidine, methadone, methohexital, mitomycin, morphine, nalbuphine, opium, oxazepam, oxycodone, oxymorphone, pentazocine, phenobarbital, porfimer, propoxyphene, resperidone, sufentanil, temazepam, thiopental, thiorzadine, tramadol, trimethaphan, and zolpidem.

27. A pharmaceutical composition comprising:
   (1) an effective amount of a bioactive compound mediating respiratory depression, muscle rigidity, and/or nausea/vomiting as an unwanted side effect thereof, with the proviso that said bioactive compound is not morphine; and
   (2) a delta receptor agonist.

28. A pharmaceutical composition comprising:
   (1) an effective amount of a bioactive compound mediating an unwanted side effect thereof; and
   (2) a non-polypeptide δ receptor activating agent effective for combating said side effect.

29. The pharmaceutical composition of claim 28, wherein the δ receptor activating agent comprises a diarylmethylpiperazine or a diarylmethylpiperdine compound.

* * * * *